US007355056B2

(12) United States Patent
Connor et al.

(10) Patent No.: US 7,355,056 B2
(45) Date of Patent: Apr. 8, 2008

(54) TRANSFECTION AGENTS

(75) Inventors: Robert Connor, Oceanside, CA (US); Joseph McAuliffe, Sunnyvale, CA (US)

(73) Assignee: Canji, Inc., San Diego, CA (US)

( * ) Notice: Subject to any disclaimer, the term of this patent is extended or adjusted under 35 U.S.C. 154(b) by 239 days.

(21) Appl. No.: 10/861,545

(22) Filed: Jun. 4, 2004

(65) Prior Publication Data

US 2005/0085427 A1    Apr. 21, 2005

Related U.S. Application Data

(60) Provisional application No. 60/475,926, filed on Jun. 4, 2003.

(51) Int. Cl.
| C07J 1/00 | (2006.01) |
| A01N 61/00 | (2006.01) |
| A01N 63/00 | (2006.01) |
| A61K 38/00 | (2006.01) |
| C07H 21/04 | (2006.01) |

(52) U.S. Cl. .............................. 552/509; 514/1; 514/44; 424/93.6; 536/5; 536/23.1; 536/23.2; 536/23.52; 536/24.5

(58) Field of Classification Search ...................... None
See application file for complete search history.

(56) References Cited

U.S. PATENT DOCUMENTS

| 5,250,524 A | 10/1993 | Kramer et al. |
| 5,264,618 A | 11/1993 | Felgner et al. |
| 5,552,309 A | 9/1996 | March |
| 5,789,244 A | 8/1998 | Engler et al. |
| 5,804,566 A | 9/1998 | Carson et al. |
| 6,013,638 A | 1/2000 | Crystal et al. |
| 6,165,779 A | 12/2000 | Engler et al. |
| 6,312,681 B1 | 11/2001 | Engler et al. |
| 6,392,069 B2* | 5/2002 | Engler et al. ............... 552/509 |
| 7,002,027 B1* | 2/2006 | Engler et al. ............... 552/549 |
| 7,163,925 B1 | 1/2007 | Jin et al. |
| 2002/0111502 A1 | 8/2002 | Engler et al. |
| 2003/0170216 A1 | 9/2003 | Ihnat et al. |
| 2003/0211598 A1 | 11/2003 | Engler et al. |
| 2004/0014709 A1 | 1/2004 | Engler et al. |
| 2005/0025742 A1 | 2/2005 | Engler et al. |
| 2005/0085427 A1 | 4/2005 | Connor et al. |
| 2005/0287119 A1 | 12/2005 | Benedict |
| 2006/0199782 A1 | 9/2006 | Engler et al. |

FOREIGN PATENT DOCUMENTS

| WO | WO 93/00052 A1 | 1/1993 |
| WO | WO 95/10265 A1 | 4/1995 |
| WO | WO 95/11984 A1 | 5/1995 |
| WO | WO 95/29186 A1 | 11/1995 |
| WO | WO 96/10038 | 4/1996 |
| WO | WO 97/05209 A1 | 2/1997 |
| WO | WO 2004/108893 A2 | 12/2004 |

OTHER PUBLICATIONS

Associated Press Release, "One way to kill cancer: give it a cold" *The Augusta Chronicle*, May 20, 1997 (accessed by PTO on World Wide Web at CNN.com on May 22, 1997).
Aungst, B.J. and N. Rogers, "Comparison of the effects of various transmucosal absorption promoters on buccal insulin delivery" *Int'l. J. Pharmaceutics*; vol. 53; pp. 227-235 (1989).
Bass, C. et al., "Recombinant adenovirus-mediated gene transfer to genitourinary epithelium in vitro and in vivo" *Cancer Gene Therapy* vol. 2; No. 2; pp. 97-104 (1995).
Benedict, W. et al., "Intravesical Ad-IFNα causes marked regression of human bladder cancer growing orthotopically in nude mice and overcome resistence to IFN-α protein" *Mol. Ther.*, vol. 10(3): pp. 525-532 (2004).
Blaese, M. et al., "Vectors in cancer therapy: how will they deliver?" *Cancer Gene Therapy*, vol. 2, No. 4; pp. 291-297 (1995).
Boulikas, "Gene therapy of prostate cancer: p53, suicidal genes, and other targets" *Anticancer Research* 17:1471-1506 (1997).
Bramson, J.L. et al., "The use of adenoviral vectors for gene therapy and gene transfer in vivo" *Current Opinion in Biotechnology*, vol. 6, pp. 590-595 (1995).
Brewster, S. et al., "Gene therapy in urological oncology: principles strategies and potential" *Eur. Urol.* vol. 25, pp. 177-182 (1994).
CALBIOCHEM Biochemical/Immunochemical 1992 Catalog, Calbiochem Biochemicals, 1-800-854-3417 (1992).
Chester, J.D. et al., "Adenovirus-mediated gene therapy for bladder cancer: efficient gene delivery to normal and malignant human urothelial cells in vitro and ex vivo" *Gene Therapy*, vol. 10, pp. 172-179 (2003).
Connor, R.J. et al., "Identification of polyamides that enhance adenovirus-mediated gene expression in the urothellum" *Gene Therapy*, vol. 8, pp. 41-48 (2001).
Croyle, M. et al., "Development of formulations that enhance physical stability of viral vectors for gene therapy" *Gene Therapy*, vol. 8, pp. 1281-1290 (2001).
Crystal, R.G., "Transfer of genes to humans: Early lessons and obstacles to success" *Science*, vol. 270, pp. 404-410 (1995).
Culver, K.W. and R.M. Blaese, "Gene therapy for cancer" *TIG*, vol. 10, No. 5; pp. 174-178 (1994).
Descamps, V. et al., "Strategies for cancer gene therapy using adenoviral vectors" *J. Mol. Med.*, vol. 74, pp. 183-189 (1996).
Eck, S.L and J.M. Wilson, "Gene-based therapy" in The Pharmacological Basis of Therapeutics, 9th ed.; by Goodman & Gilman (eds.); pp. 77-101 (1995).

(Continued)

*Primary Examiner*—Richard Schnizer
(74) *Attorney, Agent, or Firm*—Townsend and Townsend and Crew LLP

(57) ABSTRACT

The present invention provides compounds, compositions and methods that enhance the transfer of an agent into a cell. The agents can include polypeptides, polynucleotides such as genes and antisense nucleic acids, and other molecules. In some embodiments, the agents are modulating agents that can modulate a cellular activity or function when introduced into the cell. The compounds, compositions and methods are useful for introducing agents such as genes into individual cells, as well as cells that are present as a tissue or organ.

72 Claims, 6 Drawing Sheets

OTHER PUBLICATIONS

Gardlik, R. et al., "Vectors and delivery systems in gene therapy" *Med. Sci. Monit.* 11(4):RA110-121 (2005).

Goeddel, D.V. et al., "The structure of eight distinct cloned human leukocyte interferon cDNAs" *Nature*, vol. 290, pp. 20-26 (1981).

Goncalves, M., "A concise peer into the background, initial thoughts and practices of human gene therapy" BioEssays 27:506-517 (2005).

Hjelmeland, L. et al., "A new class of nonionic detergents with a gluconamide polar group" Anal. Biochem. 130:485-490 (1983).

Horton, H. et al., "Antitumor effects of interferon-ω: in vivo therapy of human tumor xenografts in nude mice" *Cancer Res.*, vol. 59: pp. 4064-4068 (1999).

Izawa, J. et al., "Inhibition of tumorigenicity and metastasis of human bladder cancer growing in athymic mice by *interferon-β* gene therapy results partially from various antiangiogenic effects including endothelial cell apoptosis" *Clin. Cancer Res.*, vol. 8(4): pp. 1258-1270 (2002).

Janout, V. et al., "Molecular umbrellas" *J. Am. Chem. Sci.*, vol. 118, pp. 1573-1574 (1996).

Janout, V. et al., "Evidence for highly cooperative binding between molecular umbrella-spermine conjugates and DNA" *Bioconjugate Chem.*, vol. 8, pp. 891-895 (1997).

Koshida, K. et al., "Prospects for molecular research in urological oncology: bladder cancer" *Hinyokika kiyo. Acta Urologica Japonica*, vol. 47(1): pp. 815-818 (2001), abstract only.

Kuball, J. et al., "Successful adenovirus-mediated wild-type *p53* gene transfer in patients with bladder cancer by intraversical vector instillation", *J. Clin. Onc.*, vol. 20(4): pp. 957-965 (2002).

Kukowska-Latallo et al. "Efficient transfer of genetic material into mammalian cells using starburst polyamidoamine dentrimers" *Proceedings of the National Academy of Sciences*, vol. 93, No. 4, pp. 1585-1590 (1996).

Lin, L.F. et al., "A system for the enhancement of adenovirus mediated gene transfer to uro-epithelium" *J. Urol.*, vol. 168: pp. 813-818 (2002).

Marshall, E., "Gene therapy's growing pains" *Science*, vol. 269; pp. 1050-1055 (1995).

Morris, B. et al., "Adenoviral-mediated gene transfer to bladder in vivo" *J. Urol.*, vol. 152, pp. 506-509 (1994).

O'Donnel, M.A. et al., "Salvage intravescial therapy with interferon-α2B plus low dose *Bacillus Calmette-Guerin* is effective in patients with superficial bladder cancer in whom *Bacillus Calmette-Guerin* alone previously failed" *J. Urol.*, vol. 166, pp. 1300-1305 (2001).

Orkin et al., "Report and recommendations of the panel to assess the NIH investment in research on gene therapy" Issued by the U.S. National Institutes of Health, Dec. 1995.

Pagliaro, L.C. et al., "Repeated intravesical instillations of an adenoviral vector in patients with locally advanced bladder cancer: A phase I study of p53 gene therapy" *J. of Clinical Oncology*, vol. 21, No. 12. Jun. 15, 2003: pp. 2247-2253.

Parsons, C. et al., "Bladder surface glycosaminoglycans: an epithelial permeability barrier" *J. Urol.*, vol. 143, pp. 139-142 (1990).

Rosenberg, S. "The immunotherapy and gene theraphy of cancer" *J. Clin. Oncol.*, vol. 10, No. 2; pp. 180-199 (1992).

Ross, G. et al., "Gene therapy in the United States: A five-year status report" *Human Gene Therapy*, vol. 7; pp. 1781-1790 (1996).

Shawaphun, S. et al., "Chemical evidence for transbilayer movement of molecular umbrellas" *J. Am. Chem. Soc.*; vol. 121; pp. 5860-5864 (1999).

Shiau, A.L. et al., "Postoperative immuno-gene therapy of murine bladder tumor by in vivo administration of retroviruses expressing mouse interferon-γ" *Cancer Gene Therapy*, vol. 8(1): pp. 73-81 (2001).

Sutton, M. et al., "In vivo adenovirus-mediated suicide gene therapy of orthotopic bladder cancer" *Mol. Ther.*, vol. 2(3): pp. 211-217 (2000).

Takahashi, R. et al., "The retinoblastoma gene functions as a growth and tumor suppressor in human bladder carcinoma cells" *PNAS USA*; vol. 88; pp. 5257-5261 (1991).

Verma, I.M. et al., "Gene therapy- promises, problems and prospects" *Nature*, vol. 389, pp. 239-242 (1997).

Verma, I. M. and Weitzman, M., "Gene therapy: Twenty-first century medicine" Annu. Rev. Biochem. 74:711-38 (2005).

Walker, Suzanne et al. "Cationic facial amphiphiles: A promising class of transfection agents," *Proceedings of the National Academy of Sciences*, vol. 93, No. 4, pp. 1585-1590 (1996).

Wills, K. et al., "Development and characterization of recombinant adenoviruses encoding human p53 for gene therapy of cancer" *Human Gene Ther.*; vol. 5; pp. 1079-1088 (1994).

Yamashita et al.; "Syn3 provides high levels of intravescial adenoviral-mediated gene transfer for gene therapy of genetically altered urothelium and superficial bladder cancer" *Cancer Gene Therapy* 9:681-686 (2002).

Zhang, J-F. et al., "Treatment of a human breast cancer xenograft with an adenovirus vector containing an interferon gene results in rapid regression due to viral oncolysis and gene therapy" *Proc. Nat'l. Acad. Sci. USA*, vol. 93, pp. 4513-4518 (1996).

Zhou et al., "Visualizing superficial human bladder cancer cell growth in vivo by green fluorescent protein expression" *Cancer Gene Therapy*, vol. 9; pp. 681-686 (2002).

Ahmed, C.M. Iqbal et al., "Interferon α2b gene delivery using adenoviral vector causes inhibition of tumor growth in xenograft models from a variety of cancers," *Cancer Gene Therapy*, 8:788-795 (2001).

Schmolka, "A comparison of block copolymer surfactant gels," *Journal of the American Oil Chemists' Society*, 68(3):206-209 (1991).

\* cited by examiner

TRANSFECTION AGENTS

CROSS-REFERENCE TO RELATED APPLICATIONS

This application claims priority benefit of U.S. Application No. 60/475,926, filed on Jun. 4, 2003. The disclosures of U.S. Application Nos. 60/475,926 and 10/455,215, both filed on Jun. 4, 2003, and PCT Application No. PCT/US04/17788, filed Jun. 4, 2004 are hereby incorporated by reference in their entireties for all purposes.

FIELD OF INVENTION

This invention pertains to novel compounds, compositions, and methods for delivering therapeutic and other agents to cells. Genes, polypeptides, proteins and other molecules are among the agents that can be delivered using the compounds and methods of the invention. The cells can be present individually or as a biological tissue or organ.

BACKGROUND OF THE INVENTION

Delivery of a compound into a cell is a first critical step for many diagnostic and therapeutic processes. Gene therapy, for example, is a highly promising tool for therapeutic and other uses that requires delivery of a nucleic acid to a cell. For example, distinct approaches have been developed to treat neoplasms based on gene transfer methods. Methods have been developed to correct specific lesions at defined genetic loci which give rise to neoplastic transformation and progression (Spandidos et al., *Anticancer Res.* 10:1543-1554 (1990); Banerjee et al., *Cancer Res.* 52:6297-6304 (1992)). Overexpression of dominant oncogenes may be addressed using techniques to inhibit the transforming gene or gene product. Loss of tumor suppressor gene function may be approached using methods to reconstitute wild-type tumor suppressor gene function (Goodrich et al., *Cancer Res.* 52:1968-1973 (1992)). Besides these methods to achieve mutation compensation, genetic techniques have been developed to specifically and selectively eradicate tumor cells. These approaches of molecular chemotherapy rely on specific expression of toxin genes in neoplastic cells (Abe et al., *Proc Soc Exp Biol Med.* 203:354-359 (1993)). Finally, gene transfer methods have been used to achieve antitumor immunization. These methods of genetic immunopotentiation use techniques of genetic immunoregulation to enhance immune recognition of tumors. Consequently, a variety of distinct approaches have been developed to accomplish gene therapy of cancer.

A high incidence of mutations has been observed in tumor suppressor genes, such as p53 and RB, in the case of carcinoma of the bladder (Fujimoto et al., *Cancer Res.* 52:1393-1398 (1992); Cairns et al., *Oncogene* 6:2305-2309 (1991)). For such genetic lesions of tumor suppressor genes, reversion of the neoplastic phenotype can be demonstrated with replacement of the corresponding wild-type tumor suppressor gene (Spandidos, Id.; Banerjee, Id.).

Carcinoma of the bladder represents a significant source of morbidity and mortality. Bladder cancer ranks 10th in males and 12th in females in cancer related mortality (Cancer Facts and Figures, *Amer. Can. Soc.* 5:11 (1995)). Therapies available for the treatment of bladder cancer include adjuvant chemotherapy or immunotherapy, transurethral resection of superficial disease, substituent cystectomy or radiotherapy which is often combined with systemic chemotherapy. Despite these therapeutic options, overall survival has not changed appreciably. (Id.) Thus, new therapeutic modalities must be developed for the treatment of bladder cancer.

Gene therapy strategies have been developed as an alternative therapeutic approach (See for example, Brewster et al., *Eur Urol* 25:177-182 (1994); Takahashi et al., *Proc Natl Acad Sci USA* 88: 5257-5261 (1991); Rosenberg, S A, *J. Clin Oncol.* 10:180-199 (1992)). Successful treatment of cancer and other conditions in a human or other animal can depend upon an adequate amount of a therapeutic agent entering the cells, and upon a large enough proportion of target cells taking up the therapeutic agent.

Many other therapeutics and other modulating agents are polypeptides or, for example, small molecules. Again, the amount of the agent that reaches a target cell population can have a great impact on the efficacy of treatment. Therefore, a need exists for compounds and methods that can enhance the amount of an agent that is delivered to a cell or a population of cells. The present invention fulfils this and other needs.

BRIEF SUMMARY OF THE INVENTION

The present invention provides compounds, compositions and methods that can enhance delivery of an agent a cell. In one embodiment, the present invention provides delivery enhancing compounds of Formula I:

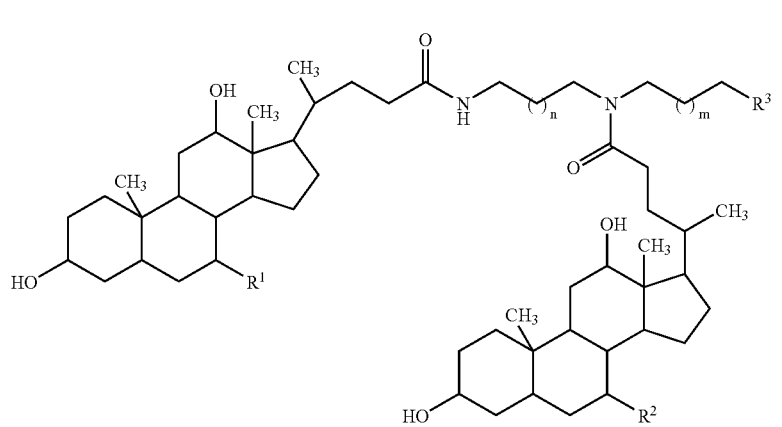

wherein:
R$^1$ and R$^2$ are each independently a member selected from the group of hydrogen, and a hydroxyl group;
m and n are each independently selected from about 0-2;
R$^3$ is selected from the group consisting of —NR$^4$R$^5$ wherein R$^4$ and R$^5$ are each independently a member selected from the group of a hydrogen, a saccharide residue, an optionally substituted alkyl, an optionally substituted acyl, an optionally substituted acyloxy, and a quaternary ammonium salt —NR$^6$R$^7$R$^8$X wherein R$^6$, R$^7$ and R$^8$ are independently a member selected from the group of hydrogen and C$_1$-C$_4$ alkyl, and X is the negatively charged ionically bound counterion selected from the group of halogen and an optionally substituted carboxylate. Also provided are methods of delivering an agent to a cell by administering a formulation that includes a delivery enhancing compound of Formula I.

In a preferred embodiment, the delivery enhancing compound of Formula I have Formula II:

protein assay. The levels of IFN present in the tissue was expressed as pg IFN/mg tissue.

FIG. 6 illustrates the amounts of IFNα2b present in tissue homogenates determined using an ELISA assay (PBL)

DETAILED DESCRIPTION OF THE INVENTION

I. Definitions

As used herein, the term "alkyl" denotes branched, unbranched, or cyclic hydrocarbon substituent or combination thereof, which may be fully saturated, mono- or polyunsaturated and can include di- and multivalent substituents, having the number of carbon atoms designated (i.e. C$_1$-C$_{10}$ means one to ten carbons) Examples of saturated hydrocarbon substituents include, but are not limited to, groups such as methyl, ethyl, n-propyl, iso-propyl, n-butyl, sec-butyl, iso-butyl, tert-butyl, octa-decyl, 2-methylpentyl, cyclohexyl,

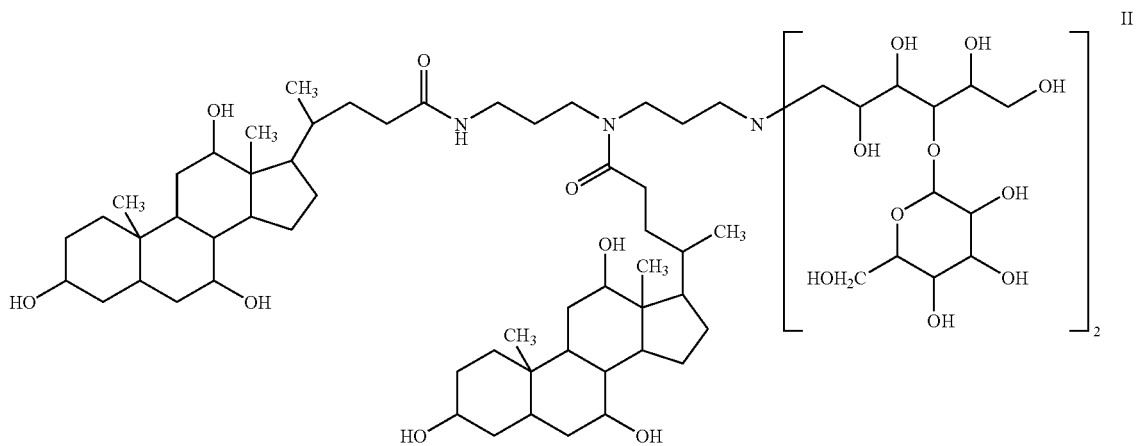

In yet another embodiment, the present invention provides compositions for delivering an agent to a cell. The compositions include the agent to be delivered and a delivery enhancing compound of Formula I.

A further aspect of the invention is a method for treating cancer, including bladder cancer, by administering to a cell a therapeutically effective amount of a therapeutic agent that is formulated in a buffer comprising a compound of Formula I.

These and other objects, aspects and advantages will be more apparent when read with the detailed description and drawings which follow.

Figure 1:
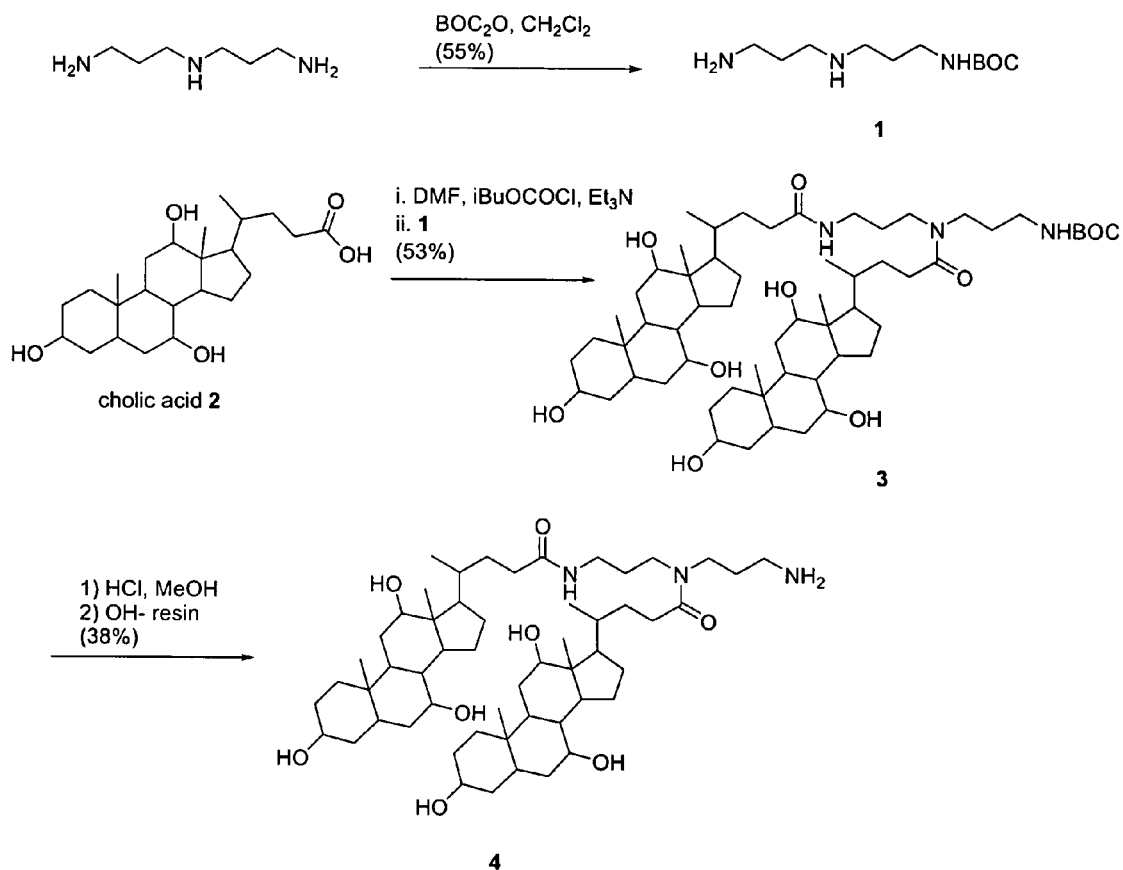
FIG. 1 depicts a synthesis of an intermediate compound useful in the synthesis of certain compounds of Formula I.

The term "aryl" means a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. The above noted aryl and heteroaryl ring systems can be further substituted with one or more functional groups which are attached commonly to such ring systems such as hydroxyl, bromo, fluoro, chloro, iodo, mercapto, thio, cyano, alkylthio, carboxyl, nitro, amino, alkoxyl, or amido.

The term "acyl" denotes the —C(O)R— substituent, wherein R is alkyl or aryl as defined above, such as but not limited to benzoyl, succinyl, acetyl, propionyl or butyryl.

The term "hydroxyl" denotes the substituent —OH—.

The term "alkoxy" denotes the substituent —OR— where R is alkyl.

The term "amino" denotes an amine linkage (—NRR') where R and R' are independently hydrogen substituent, alkyl substituent, or aryl substituent.

The term "carboxylate" denotes the substituent —OC(O)R—, wherein R is an optionally substituted alkyl or aryl.

The term "acyloxy" denotes the substituent —(CRR')$_m$C(O)OR"—, wherein R and R' are independently selected from a group comprising of an alkyl substituent, aryl substituent or hydrogen substituent and R" is hydrogen or an alkyl substituent and m is an integer between 1-8, inclusive.

The term "halogen" or "halo" refers to the substituents F, Cl, Br, or I.

The term "saccharide residue" refers to a monosaccharide substituent which can include more than one monosaccharide substituent linked as a homo-oligosaccharide substituent (an oligosaccharide comprising one type of monosaccharide) or hetero-oligosaccharide substituent (an oligosaccharide comprising more than one type of monosaccharide). In a preferred embodiment, the homo and hetero-oligosaccharide substituent is composed of 2 to 10 monosaccharide units. Monosaccharides can include pentose or hexose residues and the residues can exist as the cyclized or uncyclized (open-chain) form. When a monosaccharide is in the open chain form, the hydrogen (in an aldose) or the hydroxymethyl group (in a ketose) is remove to form a bond for attachment. Further, the oxygen atom of the carbonyl carbon can optionally be replaced with —RR'— wherein R and R' are independently selected from a bond, an alkyl, a halogen, a hydroxyl, a hydrogen, a amino substituent, and a alkoxy substituent. Preferred oligo-saccharides include a pentose-pentose disaccharide group, a hexose-hexose disaccharide group, a pentose-hexose disaccharide group, and a hexose pentose disaccharide group. The monosaccharide can be selected from a group of ribose, arabinose, xylose and lyxose, allose, altrose, glucose, mannose, gulose, idose, galactose, or talose, whereby one or more the hydroxyl groups on the monosaccharide can be replaced with hydrogen, alkyl substituent, alkoxy substituent, amino substituent, or an acyl substituent.

II. General Synthesis

The present invention provides delivery enhancing compounds and formulations that enhance transport of agents into cells, such as cells present in epithelial tissues. The compounds and formulations of the present invention can increase the amount of an agent, such as an agent that can modulate a cellular process associated with, for example, proliferation or a disease state, that enters a cell and/or increase the proportion of cells in a tissue or organ that take up the agent. Methods of delivering agents to cells using the delivery enhancing compounds of the invention are also provided.

In certain aspects, the compounds of the present invention are represented by Formula I:

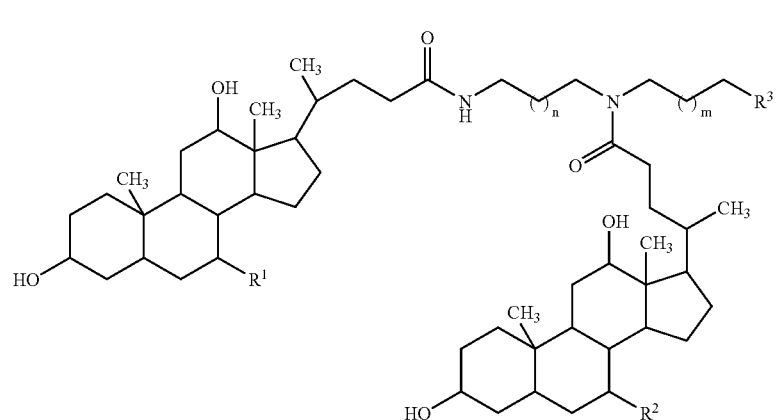

wherein:

$R^1$ and $R^2$ are each independently a member selected from the group of hydrogen, and a hydroxyl group;

m and n are each independently selected from about 0-2;

$R^3$ is selected from the group consisting of —NR$^4$R$^5$ wherein $R^4$ and $R^5$ are each independently a member selected from the group of a hydrogen, a saccharide residue, an optionally substituted alkyl, an optionally substituted acyl, and an optionally substituted acyloxy, and a quaternary ammonium salt —NR$^6$R$^7$R$^8$X, wherein $R^6$, R and $R^8$ are independently a member selected from the group of hydrogen and $C_1$-$C_4$ alkyl, and X is the negatively charged ionically bound counterion selected from the group consisting of halogen and an optionally substituted carboxylate. Preferred compounds of Formula I are set forth in Table 1.

Figure 2:
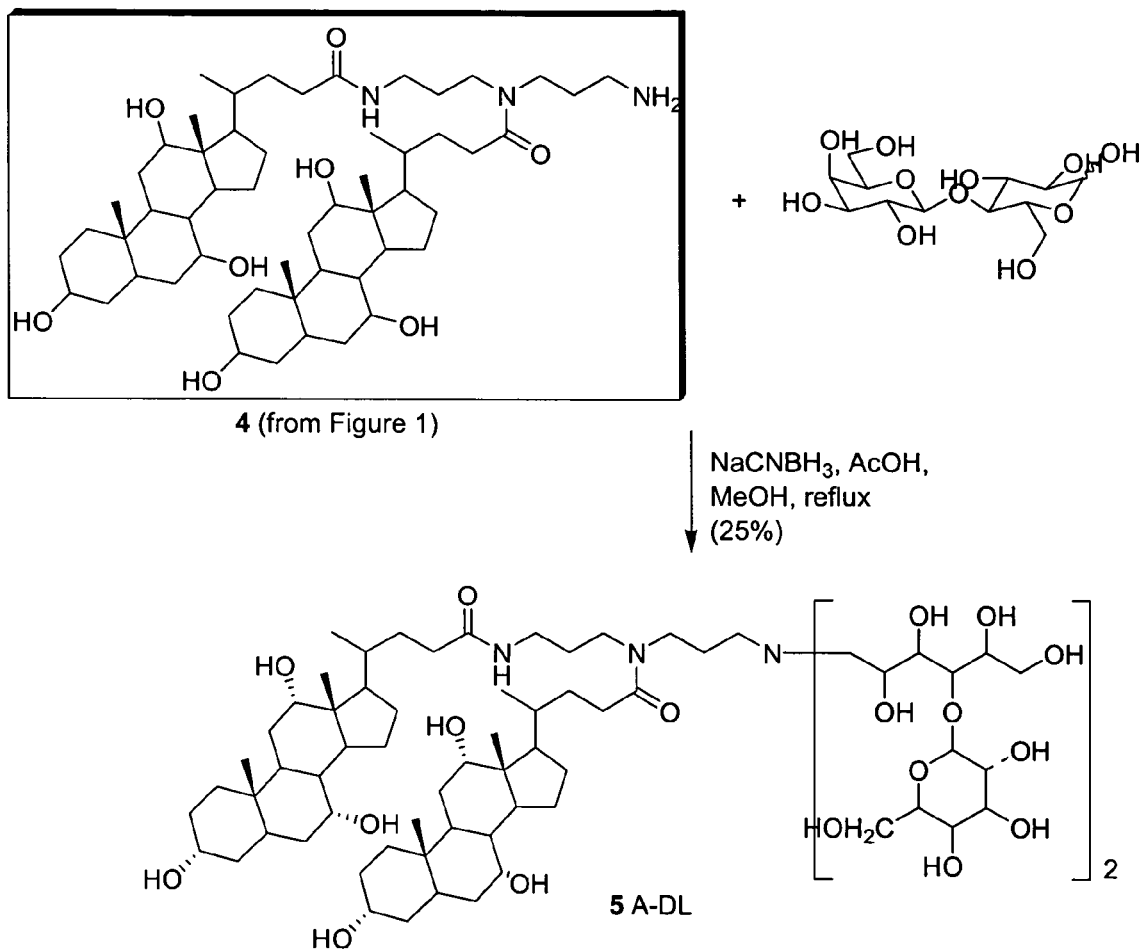
FIG. 2 depicts an attachment of a saccharide residue to an intermediate to form a compound of the present invention.

In one illustrative embodiment, compounds of Formula I can be synthesized using a generalized procedure as outlined in FIGS. 1 and 2. FIGS. 1 and 2 illustrate one particular embodiment of the present invention and thus, are merely an example and should not limit the scope of the claims herein. One of ordinary skill in the art will recognize many other variations, alternatives, and modifications that can be made to the reaction scheme illustrated in FIGS. 1 and 2. With respect to FIG. 1, cholic acid 2 is reacted with a chloroformate in the presence of an amine base, such as triethylamine, to form a mixed anhydriden intermediate. This intermediate is then reacted with a mono-protected triamine 1 to yield a cholic-amide compound 3. Treatment of the cholic-amide 3 under the acidic conditions of hydrochloric acid in a methanol solvent results in the loss of the protecting group, which in this instance is t-butoxycarbonyl, to produce a primary amine 4. FIG. 2 illustrate the coupling of the primary amine 4 and 2 equivalents of lactose under reductive amination conditions to provide the crude residue 4 which is purified by silica gel chromatography. Alternatively, and not explicitly shown in FIGS. 1 and 2, the primary amine 4 can be alkylated with an alkyl halide, such as methyl iodide or ethyl iodide, or protonated with an acid, such as hydrochloric acid or acetic acid to obtain a quaternary ammonium salt of the present invention. Such methods of making the compounds of the present invention represent certain embodiments of the present invention.

Figure 3:
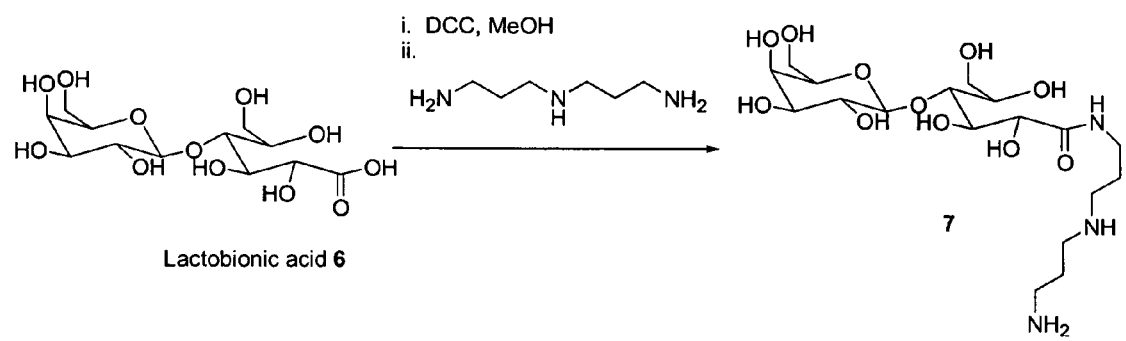
FIG. 3 depicts a synthesis of an intermediate compound useful in the synthesis of certain compounds of Formula I.
Figure 4:
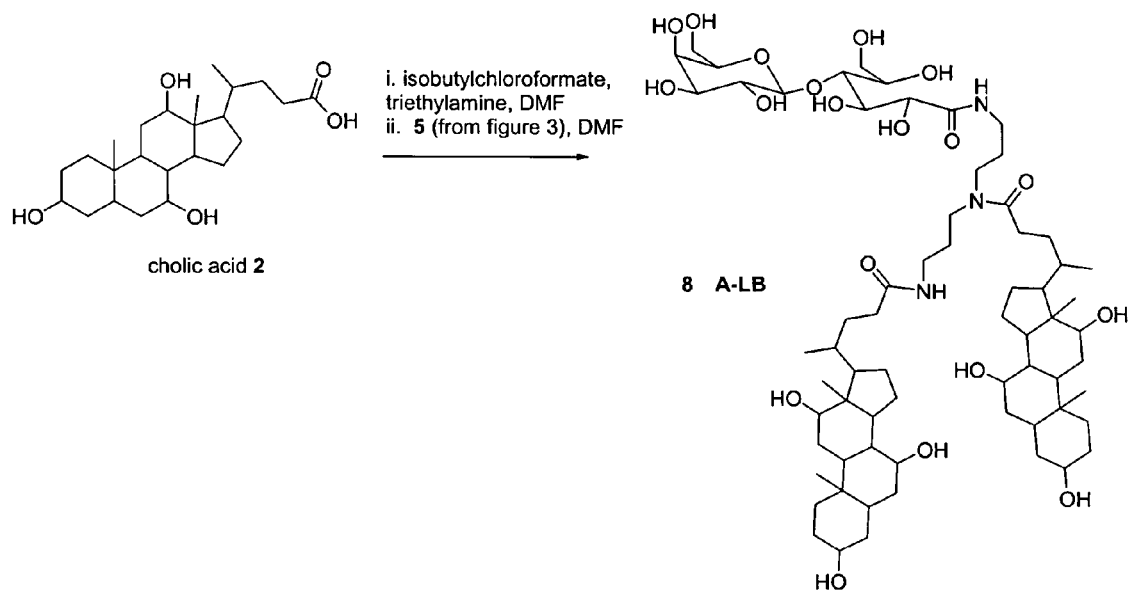
FIG. 4 depicts an attachment of a cholic acid residue to an intermediate to form a compound of the present invention.

In another illustrative embodiment, compounds of Formula I can be synthesized using a generalized procedure as outlined in FIGS. 3 and 4. FIGS. 3 and 4 illustrate one particular embodiment of the present invention and thus, are merely an example and should not limit the scope of the claims herein. One of ordinary skill in the art will recognize many other variations, alternatives, and modifications that can be made to the reaction scheme illustrated in therein. As shown in FIG. 3, a disaccharide acid 6 is coupled to a triamine using for example, dicyclohexylcarbodimide as the coupling reagent, to provide a lactobionic-diamine 7. FIG. 4 shows the formation of a mixed anhydride of cholic acid upon treatment of cholic acid 2 with a chloroformate in the presence of an amine base. Di-acylation of the lactobionic-diamine 7 was accomplished using the mixed anhydride of cholic acid as the acylating reagent to provide the crude product 8 which is purified by trituration with dichloromethane. Such methods of making the compounds of the present invention represent certain aspects of the present invention.

III. Delivery Enhancing Compounds

The present invention provides delivery enhancing compounds that, when formulated with an agent of interest, enhance delivery of the agent to a cell. In some embodiments, the cells are present in a tissue or organ. As used herein, the delivery enhancing compounds refer to a compound that enhances delivery of an agent to a cell, tissue or organ. Preferred compounds are set forth in Table 1.

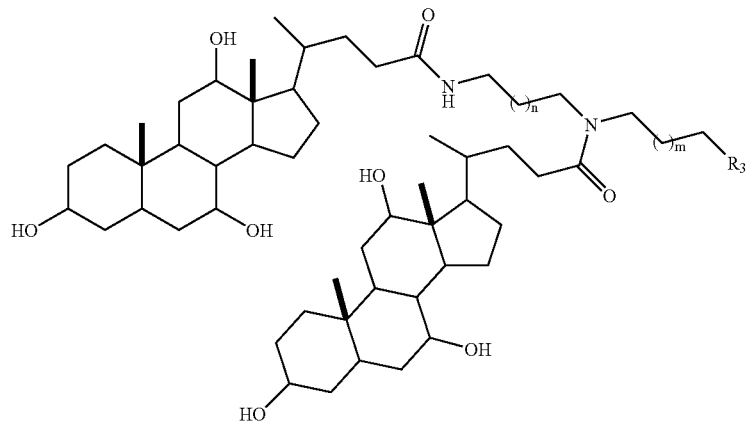

Summary of Syn3 Analogues

| R-Group | R3 | m, n = |
|---|---|---|
| A-LB Lactobionic acid (Syn3) | | 1 |

Summary of Syn3 Analogues
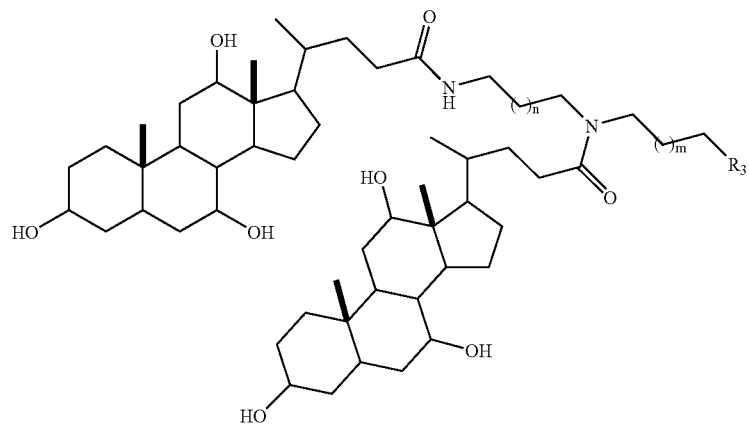
| R-Group | R3 | m, n = |
|---|---|---|
| MB Melibionic acid | 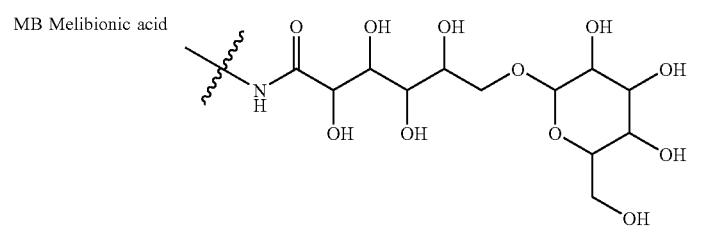 | 1 |
| MT Maltobionic acid | 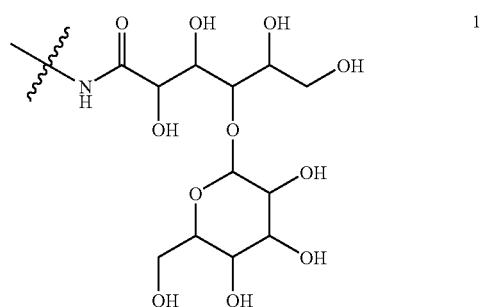 | 1 |
| A-DL Dilactose | 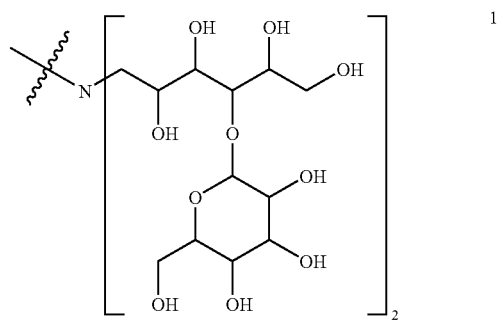 | 1 |

Summary of Syn3 Analogues
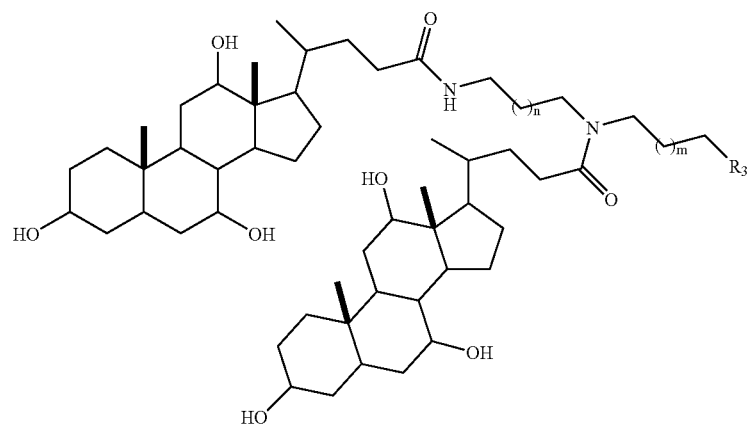
| R-Group | R3 | m, n = |
|---|---|---|
| RLB Reductive aminated lactobionic acid | (structure: lactobionic amide with galactose) | 1 |
| S-LB Short chain lactobionic acid | (structure: lactobionic amide with galactose) | 0 |
| SC Succinate | –NH–C(O)–CH$_2$CH$_2$–C(O)OH | 1 |
| TMA Trimethylammonium chloride | –N$^+$(CH$_3$)$_3$ Cl$^-$ | 1 |
| HCl Hydrochloride | –NH$_3^+$ Cl$^-$ | 1 |
| HOAc Acetate | –NH$_3^+$ OAc | 1 |

Summary of Syn3 Analogues
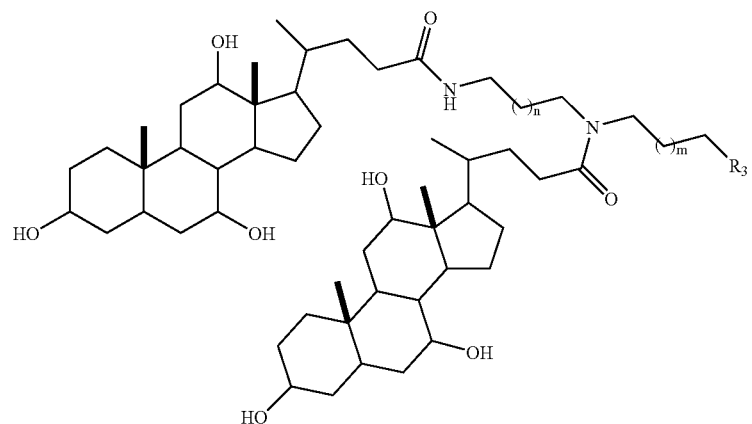
| R-Group | R3 | m, n = |
|---|---|---|
| TEA Triethylammonium chloride | [structure: -N+(Et)3 Cl-] | 1 |
| EDTA Ethylene Diamine Tetra-acetic acid | [structure: EDTA-amide] | 1 |
| DA DiAcetic acid | [structure: -N(CH2COO-Na+)2] | 1 |
| TMR Tetra-methyl Rhodamine | [structure: tetramethylrhodamine amide] | 1 |
| S-HCl Short chain hydrochloride | [structure: -NH3+ Cl-] | 0 |

Although Table 1 exemplify compounds that have a cholic acid substituent, one skilled in the art will readily recognize other steroidal substituents could replace cholic acid without compromising the delivery enhancing properties of the compound. Although an understanding of the mechanism by which enhanced delivery occurs is not essential to practicing the invention, it is noted that enhanced delivery can occur by any of various mechanisms. One such mechanism may involve the disruption of the protective glycosaminoglycan (GAG) layer on the epithelial surface of the tissue or organ by the delivery enhancing compound. Especially preferred compounds are compounds of formulae II and III set forth below.

relative to the amount of agent delivered to the cells when administered in the absence of the delivery enhancing compound. "Enhanced delivery" as used herein refers to either or both of an increase in the number of copies of an agent that enter each cell or a increase in the proportion of cells in, for example, a tissue or organ, that take up the agent. In preferred embodiments, the delivery enhancing compound results in at least about a 20% increase, more preferably at least about a 50% increase, and most preferably at least about a 100% increase in delivery of an agent to a cell or population of cells compared to the amount of the agent delivered when administered to cells in the absence of the delivery enhancing compound.

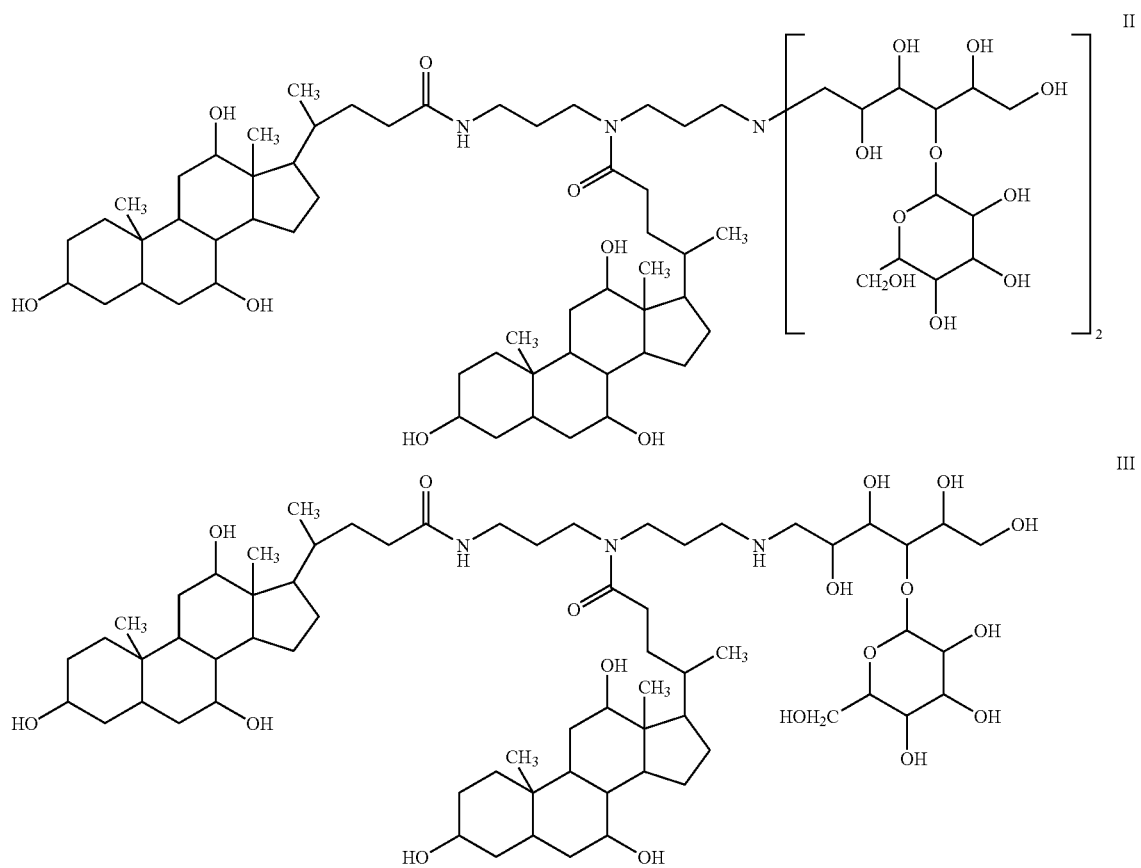

The delivery enhancing compounds and methods of the invention are useful for many applications that require delivery of a molecule to a cell. For example, diagnosis and/or treatment of many disease states often requires entry of an agent into a cell that is involved in the disease process. Another example is the use of recombinant DNA technology to produce proteins of interest, either in cell culture or in a recombinant organism. Many additional examples of situations in which it is desirable to introduce a compound into a cell are known to those of skill in the art. The compounds and methods of the invention can improve the effectiveness of each of these applications due to the increased delivery of an agent of interest to a target cell or tissue.

Administering an agent to a cell in a formulation that includes a delivery enhancing compound results in an increase in the amount of agent that is delivered to the cells, One can measure whether a particular compound or formulation is effective in enhancing delivery of an agent, such as a therapeutic or diagnostic agent, to cells by various means known to those of skill in the art. For example, a detection reagent can be included in a delivery enhancing formulation that is administered to the target cells. The amount of detection reagent present in cells that are treated with the delivery enhancing formulation is compared to that detected in cells treated with a formulation that does not include a delivery enhancing compound. As an example, where the agent of interest is a gene or a vector that includes a gene, one can include in the formulation a reporter gene for which expression is readily detectable. Where the modulating agent is a polypeptide, one can test the delivery enhancing compounds by, for example, attaching a label to the polypeptide that is present in the delivery enhancing formulation and detecting the presence and amount of label that is found in target cells after administration of the formulation. Similarly, where molecules other than polypeptides and polynucleotides are to be used as the modulating agent, one can label the molecules and detect the amount of label that enters the target cell population.

Saccharide groups that can be used in the delivery enhancing compounds of the present invention can be monosaccharides or can include more than one monosaccharide linked in either homo-oligosaccharides or hetero-oligosaccharides. Preferred monosaccharides include pentose and/or hexose residues. For example, the saccharide groups can be selected from the group of pentose monosaccharide groups, hexose monosaccharide groups, pentose-pentose disaccharide groups, hexose-hexose disaccharide groups, pentose-hexose disaccharide groups, and hexose-pentose disaccharide groups.

In some embodiments, the delivery enhancing compounds of Formula I have $R^3$ as saccharide residue that are composed of three or more monosaccharides. Preferably, the saccharide group has between one and ten monosaccharides, more preferably between one and four monosaccharides, and most preferably about two to three monosaccharides. The use of a trisaccharide, for example, can provide a compound having increased solubility.

For some applications, it is desirable to use delivery enhancing compounds that exhibit increased water solubility and/or delivery enhancing activity compared to other compounds. Such compounds are provided by the invention. For example, the invention provides compounds of Formula I wherein $R^3$ is a cationic group. Suitable cationic groups include, for example, tetramethyl and ammonium moieties, and salts thereof. Examples of such compounds include A-TMA and A-HCl as shown in Table 1. Other compounds with improved solubility and/or delivery enhancing activity include those in which the saccharide group or groups in compounds of Formula I are trisaccharides or longer.

In certain aspects, the present invention provides formulations that contain an agent to be delivered to a cell and a delivery enhancing compound. The concentration of the delivery enhancing compound in a formulation will depend on a number of factors such as the particular delivery enhancing compound being used, the buffer, pH, target tissue or organ and mode of administration. The concentration of the delivery enhancing compound will often be in the range of 1% to 50% (v/v), preferably 10% to 40% (v/v) and most preferably 15% to 30% (v/v). The delivery enhancing compounds of the invention are preferably used in the range of about 0.002 to 2 mg/ml, more preferably about 0.02 to 2 mg/ml, most preferably about 0.1 to 1 mg/ml in the formulations of the invention.

The delivery enhancing compounds of the invention are typically formulated in a solvent in which the compounds are soluble, although formulations in which the compounds are only partially solubilized are also suitable. Phosphate buffered saline (PBS) is one example of a suitable solubilizing agent for these compounds, and others are known to those of skill in the art. One will recognize that certain additional excipients and additives may be desirable to achieve solubility characteristics of these agents for various pharmaceutical formulations. For example, well known solubilizing agents such as detergents, fatty acid esters, surfactants can be added in appropriate concentrations so as to facilitate the solubilization of the compounds in the various solvents to be employed. Where the formulation includes a detergent, the detergent concentration in the final formulation administered to a patient is preferably about 0.5-2× the critical micellization concentration (CMC). Suitable detergents include those listed above.

IV. Modulatory Agents

The delivery-enhancing compounds of the invention are useful for enhancing the delivery of modulatory agents, including proteins, antibodies nucleic acids, antisense RNA, small molecules, and the like, to cells. For example, the delivery enhancing compounds are useful for delivering agents to cells that are part of any tissue or organ, including those that have an epithelial membrane.

Among the agents that are suitable for delivery using the delivery enhancing compounds (e.g., penetration enhancing compounds) are "modulatory agents," which, as used herein, refers to agents that can modulate biological processes. Such processes include, for example, cell growth, differentiation, proliferation (including neoplastic disorders such as cancer), regulation, metabolic or biosynthetic pathways, gene expression, and the like. Modulatory agents can also influence, for example, immune responses (including autoimmune disorders), infection by bacterial and fungal pathogens, and any other biological process that is regulatable by introduction of a modulatory agent.

Therapeutic agents are an example of modulatory agents that one can deliver using the delivery-enhancing agents. Such agents are useful for modulating cellular processes that are associated with disease. The term "therapeutic agent" as used herein includes, but is not limited to, therapeutic proteins, antibodies, therapeutic genes, vectors (plasmid or viral vectors) containing a therapeutic gene, antisense nucleic acids, or other therapeutic nucleic acid sequences (e.g., triplex nucleic acids). For purposes of the present invention, the term "therapeutic gene," refers to a nucleic acid sequence introduced into a cell to achieve a therapeutic effect. Examples of such therapeutic genes include, but are not limited to, tumor suppressor genes, suicide genes, antisense nucleic acid molecules, triplex forming nucleic acid molecules, genes encoding cytokines, genes encoding Type I and Type II interferons such as interferon-α, interferon-β, interferon-δ, and interferon-γ, genes encoding interleukins (e.g., IL-1, IL-2, IL-4, Il-6, IL-7 and IL-10), and colony stimulating factors such as GM-CSF. In some instances, the therapeutic gene may present in a naturally occurring or recombinantly modified virus. In addition to the foregoing genes, their therapeutic proteins, that is, the proteins and or polypeptides encoded by the genes are also within the scope of the present invention. Examples of such therapeutic proteins include, but are not limited to, cytokines, Type I and Type II interferons such as interferon-α, interferon-β, interferon-δ, and interferon-γ, interleukins (e.g., IL-1, IL-2, IL-4, Il -6, IL-7 and IL-10), and colony stimulating factors such as GM-CSF. In certain other instances, the antibodies, such as the antibodies of the foregoing proteins, are modulatory agents of the present invention. These include, but are not limited to, antibodies to Type I and Type II interferons such as anti-interferon-α, anti-interferon-β, anti-interferon-δ, anti-interferon-γ, and the anti-interleukins (e.g., anti-IL-1, anti-IL-2, anti-IL-4, anti-Il-6, anti-IL-7 and anti-IL-10).

In certain embodiments, the interferon polypeptide or antibody is Type I or Type II interferon, including those commonly designated as alpha-interferon, beta-interferon, gamma-interferon, and omega-interferon (e.g., α-interferon, β-interferon, γ-interferon and ω-interferon), and combinations thereof, including the consensus sequence for alpha-interferon. In some embodiments, the alpha-interferon is $alpha_1$ or $alpha_2$-interferon. In some embodiments, the protein is interferon α-2b or anti-interferon α-2b. Other interferons include interferon α-2β, a fusion interferon α-/2α-1, interferon α-2e, human α1 or α2 interferon.

In some embodiments, the interferon is a hybrid interferon. The construction of hybrid alpha-interferon genes containing combinations of different interferon subtype sequences (e.g., α and Δ, α and β, and α and F) is disclosed in U.S. Pat. Nos. 4,414,150, 4,456,748, and 4,678,751. U.S. Pat. Nos. 4,695,623, 4,897,471 and 5,831,062 disclose novel human leukocyte interferon polypeptides having amino acid sequences which include common or predominant amino acids found at each position among naturally-occurring alpha interferon subtype polypeptides and are referred to as consensus human leukocyte interferon. In one embodiment of the invention, the hybrid interferon is interferon α2 α1.

In one embodiment, the interferon is an interferon-α. Recombinant interferon alphas, for instance, have been cloned and expressed in *E. coli* (e.g., Weissmann et al., *Science*, 209:1343-1349 (1980); Sreuli et al., *Science*, 209: 1343-1347 (1980); Goeddel et al., *Nature*, 290:20-26 (1981); Henco et al., *J. Mol. Biol.*, 185:227-260 (1985)). In some embodiments, the interferon is a human interferon alpha. In some embodiments, the interferon alpha is interferon alpha 2a or 2b.

The term interferon as used herein is intended to include all classes and subclasses of interferon, and deletion, insertion, or substitution variants as well as proteins, polypeptides and antibodies. In one embodiment, the interferon gene/protein is the interferon-α gene/protein. Recombinant interferon alphas, for instance, have been cloned and expressed in *E. coli* by several groups (for example, Weissmann et al., *Science*, 209:1343-1349 (1980); Sreuli et al., *Science*, 209:1343-1347 (1980); Goeddel et al., *Nature*, 290:20-26 (1981); Henco et al., *J. Mol. Biol.*, 185:227-260 (1985)). In some embodiments, the interferon gene of the system is derived from the human nucleotide or polypeptide sequence. The human interferon alphas, for example, are a family of proteins comprising at least 24 subspecies (Zoon, K. C., *Interferon*, 9:1 (1987), Gresser, I., ed., Academic Press, NY). The interferon alphas were originally described as agents capable of inducing an antiviral state in cells but are now known as pleiotropic lymphokines affecting many functions of the immune system (Openakker et al., *Experimentia*, 45:513 (1989)). In some embodiments, the interferon alpha is interferon alpha 2a or 2b (see, for example, WO 91/18927), although any interferon alpha may be used.

Pharmaceutical compositions of the interferon IFN-α (i.e., alpha interferon or interferon alpha) gene, protein or antibody, have many therapeutic indications, including hairy cell leukemia, kaposi's sarcoma, renal cell carcinoma, non Hodgkin's lymphoma, T-cell leukemia, multiple and chronic myelogenous leukemia, malignant melanoma, bladder cell carcinoma, colon carcinoma (with 5-FU), condyloma acuminata, rhinovirus and various forms of chronic viral hepatitis occurring as a result of hepatitis B virus (HBV), hepatitis C virus (HCV), non A non B virus (NANB) hepatitis, or hepatitis δ virus (HDV) infection (Pestka, *AIDA Research & Human Retroviruses*, 8(5):776-786 (1992)). IFN-α has also been found to be highly effective against megakaryocytopoiesis and controlling thrombocytosis in patients with myeloproliferative disorders (Talpaz et al., *Annals Int. Med.*, 99:789-792 (1983); Gisslinger et al., Lancet, i:634-637 (1989); Ganser et al., *Blood*, 70:1173-1179 (1987)).

In some embodiments, the compositions of the invention comprise a "therapeutically effective" amount of a therapeutic agent in a buffer comprising a delivery-enhancing compound. "Therapeutically effective" as used herein refers to the prevention of, reduction of, or curing of symptoms associated with a disease state.

The delivery-enhancing agents and formulations that contain these agents can also be used to facilitate delivery of genes, proteins or antibodies of interest to cells, in particular cells of organs and tissues. These genes can encode, for example, proteins that are of interest for commercial purposes. As an example, one can use the agents and formulations to deliver to mammary tissue of a mammal a gene that encodes a nutritionally important protein which is then secreted in the milk produced by the mammal. Other uses of such agents and formulations will be evident to those of skill in the art.

The delivery enhancing agents and formulations that include such agents are also useful for delivering diagnostic agents to cells, organs and tissues. Examples of diagnostic agents include marker genes that encode proteins that are readily detectable when expressed in a cell (including, but not limited to, β-galactosidase, green fluorescent protein, luciferase, and the like) and labeled nucleic acid probes (e.g., radiolabeled probes).

V. Vectors for Gene Delivery

In the situation where an agent to be delivered to a cell is a gene, one can incorporate the gene into a vector. Examples of vectors used for such purposes include expression plasmids capable of directing the expression of the gene of interest in the target cell. In other instances, the vector is a viral vector system wherein the gene of interest is incorporated into a viral genome capable of transfecting the target cell. Where the gene of interest is designed for expression in a target cell, the gene can be operably linked to expression and control sequences that can direct expression of the gene in the desired target host cells. Thus, one can achieve expression of the gene under appropriate conditions in the target cell.

Viral vector systems useful in the practice of the instant invention include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, genes of interest are inserted into such vectors to allow packaging of the gene construct, typically with accompanying viral DNA, infection of a sensitive host cell, and expression of the gene of interest. A preferred recombinant viral vector is the adenoviral vector delivery system which has a deletion of the protein IX gene (see, International Patent Application WO 95/11984, which is herein incorporated by reference in its entirety for all purposes).

"Recombinant" as used herein refers to nucleic acids and the proteins encoded by them wherein the nucleic acids are constructed by methods of recombinant DNA technology, also termed "genetic engineering".

Therapeutically effective amounts of the pharmaceutical composition comprising a modulatory gene, such as a p53 gene or a retinoblastoma tumor suppressor gene, in a recombinant viral vector delivery system formulated in a buffer comprising a delivery-enhancing agent, will be administered in accord with the teaching of this invention. For example, therapeutically effective amounts of a therapeutic gene in the recombinant adenoviral vector delivery system formulated in a buffer containing a delivery-enhancing agent are in the range of about $1\times10^8$ particles/ml to $1\times10^{12}$ particles/ml, more typically about $1\times10^8$ particles/ml to $5\times10^{11}$ particles/ml, most typically $1\times10^9$ particles/ml to $1\times10^{11}$ particles/ml (PN/ml).

VI. Gene Delivery Systems

As used herein, "gene delivery system" refers to any means for the delivery of an agent to a target cell. The agent can be associated with a gene delivery system which is then delivered to the cell using a formulation that contains a delivery enhancing compound.

In some embodiments of the invention, gene constructs or other agents are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, gene constructs can be linked through a polylysine moiety to asialo-oromucoid, which is a ligand for the asialoglycoprotein receptor of hepatocytes.

Similarly, viral envelopes used for packaging gene constructs can be modified by the addition of receptor ligands or antibodies specific for a receptor to permit receptor-mediated endocytosis into specific cells (see, e.g., WO 93/20221, WO 93/14188, WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88: 8850-8854 (1991)). In other embodiments, molecular conjugates of the instant invention can include microtubule inhibitors (WO/9406922); synthetic peptides mimicking influenza virus hemagglutinin (Plank et al., *J. Biol. Chem.* 269:12918-12924 (1994)); and nuclear localization signals such as SV40 T antigen (WO93/19768).

In some embodiments of the invention, the modulating agent is an antisense nucleic acid. The antisense nucleic acid can be provided as an antisense oligonucleotide (see, e.g., Murayama et al., *Antisense Nucleic Acid Drug Dev.* 7:109-114 (1997)). Genes encoding an antisense nucleic acid can also be provided; such genes can be formulated with a delivery enhancing compound and introduced into cells by methods known to those of skill in the art. For example, one can introduce a gene that encodes an antisense nucleic acid in a viral vector, such as, for example, in hepatitis B virus (see, e.g., Ji et al., *J. Viral Hepat.* 4:167-173 (1997)); in adeno-associated virus (see, e.g., Xiao et al., *Brain Res.* 756:76-83 (1997)); or in other systems including, but not limited, to an HVJ (Sendai virus)-liposome gene delivery system (see, e.g., Kaneda et al., *Ann. N.Y. Acad. Sci.* 811: 299-308 (1997)); a "peptide vector" (see, e.g., Vidal et al., *CR Acad. Sci III* 32:279-287 (1997)); as a gene in an episomal or plasmid vector (see, e.g., Cooper et al., *Proc. Natl. Acad. Sci. U.S.A.* 94:6450-6455 (1997), Yew et al. *Hum Gene Ther.* 8:575-584 (1997)); as a gene in a peptide-DNA aggregate (see, e.g., Niidome et al., *J. Biol. Chem.* 272:15307-15312 (1997)); as "naked DNA" (see, e.g., U.S. Pat. No. 5,580,859 and U.S. Pat. No. 5,589,466); in lipidic vector systems (see, e.g., Lee et al., *Crit Rev Ther Drug Carrier Syst.* 14:173-206 (1997)); polymer coated liposomes (Marin et al., U.S. Pat. No. 5,213,804, issued May 25, 1993; Woodle et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al, U.S. Pat. No. 5,279,833, issued Jan. 18, 1994; Gebeyehu et al., U.S. Pat. No. 5,334, 761, issued Aug. 2, 1994); gas filled microspheres (Unger et al., U.S. Pat. No. 5,542,935, issued Aug. 6, 1996), ligand-targeted encapsulated macromolecules (Low et al. U.S. Pat. No. 5,108,921, issued Apr. 28, 1992; Curiel et al., U.S. Pat. No. 5,521,291, issued May 28, 1996; Groman et al., U.S. Pat. No. 5,554,386, issued Sep. 10, 1996; Wu et al., U.S. Pat. No. 5,166,320, issued Nov. 24, 1992).

VII. Protein Delivery Systems

As used herein, "protein delivery system" refers to any means for the delivery of an agent to a target cell. The agent can be associated with a protein delivery system which is then delivered to the cell using a formulation that contains a delivery enhancing compound. The protein and the delivery enhancing compound can be delivered in a simultaneous manner, or in combination wherein the protein is administered first, followed by the delivery enhancing agent, as well as wherein the delivery enhancing agent is delivered first, followed by the protein.

Various systems include, for example, liposome delivery systems, direct injection or contacting, polymer coated liposomes, cationic liposomes, gas filled microspheres, ligand-targeted encapsulated macromolecules, patches and other conventional protein delivery platforms.

VIII. Pharmaceutical Formulations

When used for pharmaceutical purposes, the formulations of the invention include a buffer that contains the delivery-enhancing compound. The buffer can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. (1966) *Biochemistry* 5:467. The pH of the buffer in the pharmaceutical composition comprising a modulatory gene contained in an adenoviral vector delivery system, for example, is typically in the range of 6.4 to 8.4, preferably 7 to 7.5, and most preferably 7.2 to 7.4.

The compositions of the present invention can additionally include a stabilizer, enhancer or other pharmaceutically acceptable carriers or vehicles. A pharmaceutically acceptable carrier can contain a physiologically acceptable compound that acts, for example, to stabilize the recombinant adenoviral vector delivery system comprising the tumor suppressor gene. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier depends on the route of administration and the particular physio-chemical characteristics of the recombinant adenoviral vector delivery system and the particular tumor suppressor gene contained therein. Examples of carriers, stabilizers or adjuvants can be found in Martin, *Remington's Pharm. Sci.,* 15th Ed. (Mack Publ. Co., Easton, Pa. 1975), which is incorporated herein by reference.

IX. Administration of Formulations

In some embodiments, the delivery-enhancing compound is included in the buffer in which the modulating agent is formulated. The delivery-enhancing compound can be administered prior to the modulating agent or concomitant with the modulating agent. In some embodiments, the delivery-enhancing compound is provided with the modulating agent by mixing a modulating agent preparation with a delivery-enhancing compound formulation just prior to administration to the patient. In other embodiments, the delivery-enhancing compound and modulating agent are provided in a single vial to the caregiver for administration.

In the case of a pharmaceutical composition comprising a tumor suppressor gene contained in a recombinant adenoviral vector delivery system formulated in a buffer which further comprises a delivery-enhancing agent, the pharmaceutical composition can be administered over time in the range of about 5 minutes to 3 hours, preferably about 10 minutes to 120 minutes, and most preferably about 15 minutes to 90 minutes. In another embodiment the delivery-enhancing agent may be administered prior to administration of the recombinant adenoviral vector delivery system containing the tumor suppressor gene. The prior administration of the delivery-enhancing agent may be in the range of about 30 seconds to 1 hour, preferably about 1 minute to 10 minutes, and most preferably about 1 minute to 5 minutes prior to administration of the adenoviral vector delivery system containing the tumor suppressor gene.

The modulating agent formulated in a buffer comprising a delivery-enhancing agent can be delivered to any tissue or organ, including neoplastic tissues such as cancer tissue, using any delivery method known to the ordinarily skilled artisan for example, intratumoral or intravesical administration. Tissues and organs include any tissue or organ having an epithelial membrane such as the gastrointestinal tract, the bladder, respiratory tract, and the lung. Examples include but are not limited to carcinoma of the bladder and upper respiratory tract, vulva, cervix, vagina or bronchi; local metastatic tumors of the peritoneum; broncho-alveolar carcinoma; pleural metastatic carcinoma; carcinoma of the mouth and tonsils; carcinoma of the nasopharynx, nose, larynx, oesophagus, stomach, colon and rectum, gallbladder, or skin; or melanoma.

In some embodiments of the invention, the therapeutic agent is formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701. Such formulations are especially useful for the treatment of cancers of the mouth, head and neck cancers (e.g., cancers of the tracheobronchial epithelium) skin cancers (e.g., melanoma, basal and squamous cell carcinomas), cancers of the intestinal mucosa, vaginal mucosa, and cervical cancer.

In some embodiments of the invention, a therapeutic agent is formulated in ophthalmic formulations for administration to the eye. Such formulations are useful in the delivery of the retinoblastoma (RB) gene to the eye, optionally in conjunction with the delivery of p53.

X. Methods of Treatment

The formulations of the invention are typically administered to enhance transfer of an agent to a cell. The cell can be provided as part of a tissue, such as an epithelial membrane, or as an isolated cell, such as in tissue culture. The cell can be provided in vivo, ex vivo, or in vitro.

The formulations containing delivery enhancing compounds and modulating agents can be introduced into the tissue of interest in vivo or ex vivo by a variety of methods. In some embodiments of the invention, the modulating agent is introduced to cells by such methods as microinjection, calcium phosphate precipitation, liposome fusion, or biolistics. In further embodiments, the therapeutic agent is taken up directly by the tissue of interest.

In some embodiments of the invention, the compositions of the invention are administered ex vivo to cells or tissues explanted from a patient, then returned to the patient. Examples of ex vivo administration of therapeutic gene constructs include Arteaga et al., Cancer Research 56(5): 1098-1103 (1996); Nolta et al., Proc Natl. Acad. Sci. USA 93(6):2414-9 (1996); Koc et al., Seminars in Oncology 23 (1):46-65 (1996); Raper et al., Annals of Surgery 223(2): 116-26 (1996); Dalesandro et al., J. Thorac. Cardi. Surg., 11(2):416-22 (1996); and Makarov et al., Proc. Natl. Acad. Sci. USA 93(1):402-6 (1996). In one embodiment, the present invention provides a method for treating bladder cancer by the administration of a modulatory agent, such as a protein or antibody in combination with SYN-3.

EXAMPLES

The following examples are intended to illustrate, not limit the scope of this invention. In the following examples, "g" means grams, "ml" means milliliters, "mol" means moles, "° C." means degrees Centigrade, "min." means minutes, "DMF" means dimethylformamide. All temperatures are in degrees Centigrade unless otherwise specified.

Example 1

Synthesis of Compound A-DL (see FIGS. 1 and 2)

The following relates the methodology utilized in the synthesis of compound 5, also know as A-DL. Provided below are the synthetic details for compounds 1, 3-5 and the steps used for purification.

A. Materials and Reagents Used
t-butyloxycarbonyl anhydride
N-(3-aminopropyl)-1,3-diaminepropane
cholic acid
isobutyl chloroformate
triethylamine
sodium cyanoborohydride
lactose
5% hydrochloric acid
acetic acid B. Experimental Procedure Compound 1: A solution of t-butyloxycarbonyl anhydride (10.0 mmol) in $CH_2Cl_2$ (50 mL) was added dropwise to a well stirred solution of N-(3-aminopropyl)-1,3-diaminepropane (50-mmol) in $CH_2Cl_2$ (150 mL) at 5° C. over 20 minutes. The mixture was stirred for 2 h after which the solvent was removed and the resulting residue was redissolved in $H_2O$ (200 mL). This aqueous solution was then extracted with $CH_2Cl_2$ (8*50 mL). TLC was performed using $MeCN:AcOH:H_2O$ (4:1:1) with the product having an rf of 0.35, and phosphomolybdic acid used for detection. Initial extracts containing non-polar impurities were discarded. The desired organic extracts were pooled, dried over $NaSO_4$ and concentrated to give the desired N-BOC amine, 1 (5.53 mmol, 55% with respect to BOCO).

Compound 3: Cholic acid 2 (8.94 mmol) in DMF (80 mL) was treated with isobutyl chloroformate (9.25 mmol) and triethylamine (14.3 mmol) at 5° C. for 10 minutes. Compound 1 (3.57 mmol) was then added and the mixture was allowed to stir for 72 h at room temperature. The reaction was monitored via TLC using $CH_2Cl_2:MeOH$ (3:1) with the desired product having an rf of 0.35. Evaporation of the solvent was followed by purification on a silica column (100 g silica, using $CH_2Cl_2:MeOH$ (5:1)) provided compound 2 (1.90 mmol 53%).

Compound 4: Compound 3 (1.90 mmol) was dissolved in a 5% solution of HCl in MeOH (50 mL) and allowed to stir at room temperature for 15 h. The reaction was monitored with TLC ($CH_2Cl_2:MeOH$ (3:1)) with the desired product having an rf of 0.5. The solvent was co-evaporated with toluene and redissolved in MeOH. The solution was treated with base resin (IRA-400, OH⁻) and purified on silica gel using $CH_2Cl_2:MeOH:Et_3N:H_2O$ (60:30:5:5) to afford compound 3 (0.72 mmol 38%).

Compound 5 (A-DL): Compound 4 (2.48 mmol) was dissolved in MeOH (200 mL), and acetic acid (4 mL) and lactose (6.0 mmol) were added (see FIG. 2). The solution was heated to reflux followed by the addition of sodium cyanoborohydride (6.0 mmol). After 3 h, more sodium cyanoborohydride (6.0 mmol) was added and the reaction was stirred at reflux for an additional 12 h. The reaction was monitored via TLC using a 4:1:1 AcCN;AcOH:H$_2$O solvent system. Two major new compounds were observed with lower rfs (approximately 0.1 and 0.05) then compound 4 and lactose. These two spots corresponded to A-RLB and A-DL (with A-DL having the lower rf). The solvent was evaporated and the resulting residue was dissolved in 1:1 MeOH:H$_2$O solution and purified on a reverse phase silica gel column. Slowly increasing the percentage of methanol afforded unreacted compound 3 and lactose followed by the elution of A-DL and A-RLB. The fractions containing A-DL and A-RLB were pooled and concentrated. The resulting residue was purified on a silica gel column (150 g silica) using CH$_2$Cl$_2$:MeOH:H$_2$O:Et$_3$N (60:30:5:5) as the solvent. 0.26 mmol of A-RLB was recovered, along with the desired compound 5 (A-DL, 0.61 mmol 25%).

Example 2

Synthesis of Compound A-LB (Syn3) (see FIGS. 3 and 4)

The following relates the methodology utilized in the synthesis of compound 8, also known as A-LB. Provided below are the synthetic details for compound 5-6 and the steps required for purification.

A. Materials and Reagents Used
  N-(3-aminopropyl)-1,3-diaminepropane
  cholic acid
  dicyclohexylcarbodiimide (DCC)
  isobutyl chloroformate
  triethylamine
  lactobionic acid B. Experimental
  Compound 7: A solution of lactobionic acid 6 (716 mg, 2 mmol) in methanol (60 mL) was heated to reflux. To this solution was added DCC (500 mg, 2.5 mmol) and the resultant solution was stirred at reflux. After 2 h, N-(3-aminopropyl)-1,3-diaminepropane (800 mL, 5.7 mmol) was added and the resultant solution was stirred for 1 additional hour. The reaction solution was cooled to room temperature and concentrated to obtain the crude product 7. Crude amide 7 was purified upon trituration with dichloromethane to provide 7 (2.72 g, 5.7 mmol) as a sticky hygroscopic solid.
  Compound 8: A solution of cholic acid 2 (4.1 g, 10 mmol)) in DMF (60 mL) was cooled to 0° C. To this solution was added isobutyl chloroformate (1.2 mL, 10.2 mmol) and triethylamine (1.4 mL, 10.4 mmol) and the resultant solution was stirred for 10 minutes followed by addition of 5 (2.5 g, 5.3 mmol) in DMF (40 mL). The reaction solution was stirred for 72 h then concentrated to provide the crude product 8. Crude product was purified by column chromatography to provide the pure 8 (A-LB).

Example 3

Uptake of IFN Protein after Intravesical Administration in a SYN3 Formulation

This Example shows that SYN3 enhances the uptake of interferon protein by increasing the tissue levels of interferon protein when administered in a SYN3 formulation.

Methods. The hybrid IFN protein and the IFNα2b protein (Intron A) were used. For comparison purposes, the hybrid protein was also be included at the time t=0 time point. Outbred HSD rats were anesthetized using isoflurane. Pretreatment urine was collected. The bladder was trans-urethrally catheterized using a catheter and lubricant. The test article was administered to the bladder, the urethra was tied off with 2.0G suture without removing the catheter. After 45 minutes (0 hour), the test article was removed and the animal allowed to recover in the home cage. Urine samples were obtained from rats immediately before sacrifice. After the urine was collected, the bladders were harvested from the rats on that day. The tissue was frozen and assayed for up-regulation of IFN responsive genes.

| Group | Animal ID's | Sacrifice time | Urine volumes | Treatment |
|---|---|---|---|---|
| 1 | 888, 889 | 0 h post tx | — | IFN α2b protein in PBS |
| 2 | 876, 877 | 4 h post tx | 876: 1.8 ml 877: 2.3 ml | IFN α2b protein in PBS |
| 3 | 882, 883 | 1 d post tx | 882: 2.8 ml 883: 2.9 ml | IFN α2b protein in PBS |
| 4 | 890, 891, 892 | 0 h post tx | — | IFN α2b protein in SYN3: 1 mg/ml |
| 5 | 878, 879 | 4 h post tx | 878: 1.3 ml 879: 1.2 ml | IFN α2b protein in SYN3: 1 mg/ml |
| 6 | 884, 885 | 1 d post tx | 884: 0.8 ml 885: 0.8 ml | IFN α2b protein in SYN3: 1 mg/ml |
| 7 | 880, 881 | 4 h post tx | 880: 1.9 ml 881: 2.2 ml | IACB: 1 × 10$^{11}$ P/ml in SYN3: 1 mg/ml |
| 8 | 886, 887 | 1 d post tx | 886: 0.8 ml 887: 1.5 ml | IACB: 1 × 10$^{11}$ P/ml in SYN3: 1 mg/ml |

| Group | Animal ID's | Sacrifice time | Treatment |
|---|---|---|---|
| 1 | 893, 894 | 0 h post tx | IFN α2α1 protein in PBS |
| 4 | 895, 896 | 0 h post tx | IFN α2α1 protein in SYN3: 1 mg/ml |

Materials:
38 female Harlan Sprague-Dawley rats;
IACB: Tris-glycerol formulation 7.57×10$^{11}$ P/ml
IHCB: vPBS formulation 1.10×10$^{12}$ P/ml
SYN3: 6× stock (6 mg/ml)
Intron A: Reference vial used: hydrated in 1 ml of sterile nanopure dH$_2$O (10 MIU/ml)
  950 μl of Intron A diluted with 3,008 μl of PBS (2.4 MIU/ml)
  625 μl of diluted Intron A added to 125 μl of either PBS or SYN3 (6 mg/ml)
IFN α2α1 protein: 105 μg/ml=105×10$^6$ pg/ml
  1.34×10$^7$ IU/ml
  1.28×10$^8$ IU/mg
  IACB is a recombinant adenoviral vector for interferonα2b and has a CMV promoter and a E1-region deletion. IHCB is a recombinant adenoviral vector for hybrid interferon α2α1 also having a CMV promoter and a E1-region deletion.

Preparation of Test Articles:

Prepare IFNα2b at 2.4 MIU/ml final concentration (hydrate one reference vial in 1 ml sterile Water For Injection)
950 μl Intron A concentrate
3,008 μl PBS To prepare the IFNα2b in PBS:
625 μl Intron A @2.4 MIU/ml
125 μl PBS To prepare the IFNα2b in SYN3:
625 μl Intron A @2.4 MIU/ml
125 μl SYN3

To prepare the rAd-IFNα2b (IACB) in SYN3:
66 μl IACB
250 μl SYN3
1184 μl Tris-glycerol buffer Prepare concentrate of IFNα2α1 protein (2.2 ml):
243 μl IFN α2α1 protein
1957 μl PBS IFNα2α1/PBS:
625 μl IFNα2α1 protein
125 μl PBS IFNα2 α1/SYN3:
625 μl IFNα2α1 protein
125 μl SYN3

| Ingredient | Amount (mg/vial) |
|---|---|
| (SYN3) | 120 |
| Citric Acid Monohydrate USP/EP/Extra Pure or USP | 1.6 |
| Sodium Citrate Dihydrate USP/EP/Extra Pure or USP | 5.1 |
| Hydroxypropyl-β-cyclodextrin (High degree of substitution) | 1000 |
| Polysorbate 80 USP | 60 |

Figure 5:
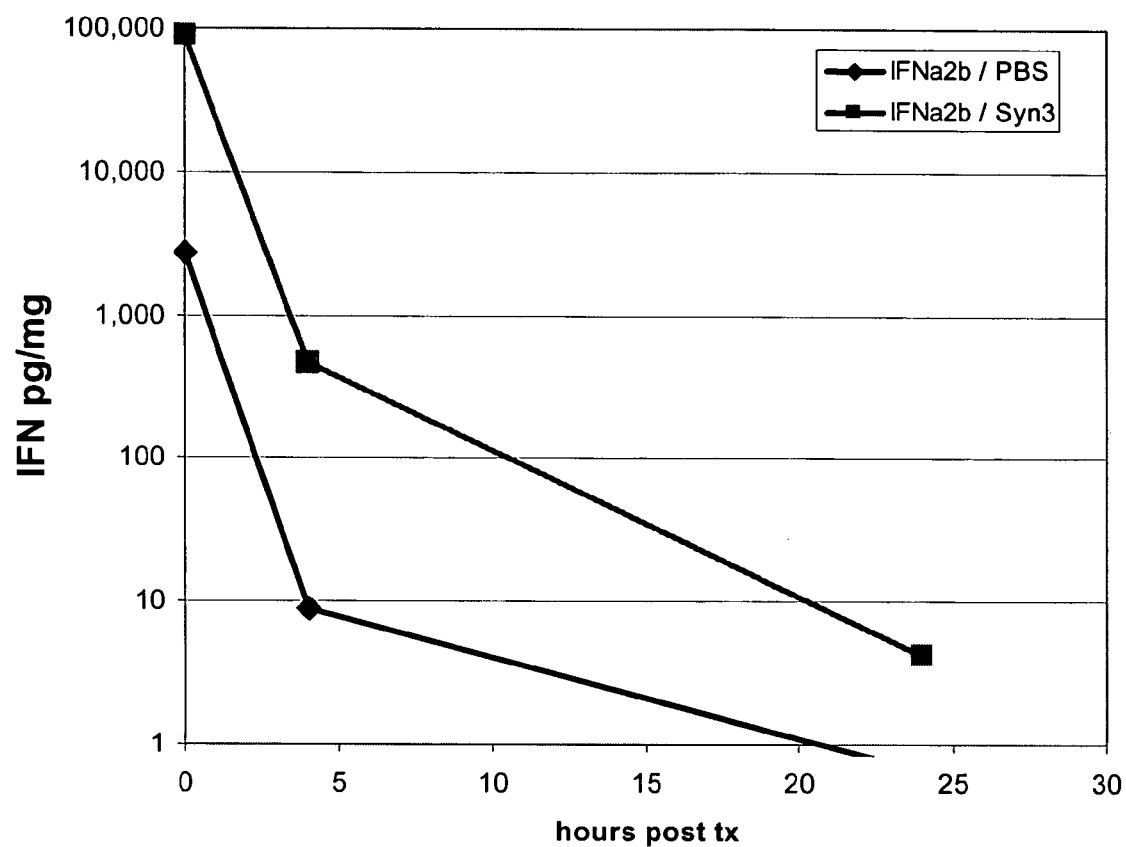
FIG. 5 illustrates the amounts of IFNα2b present in tissue homogenates determined using an ELISA assay (PBL). The concentration of protein was measured using a Bradford (cyclohexyl)methyl, cyclopentylmethyl. The substituents can be optionally substituted with one or more functional groups which are attached commonly to such chains, such as hydroxyl, bromo, fluoro, chloro, iodo, mercapto, or thio, cyano, alkylthio, aryl, heteroaryl, carboxyl, nitro, amino, alkoxyl, amido, and the like to form alkyl substituents such as carboxymethyl, trifluoromethyl, 3-hydroxyhexyl, 2-carboxypropyl, and the like. An unsaturated alkyl substituent is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The substituents can be substituted with one or more functional groups which are attached commonly to such chains as described for saturated hydrocarbons.
Figure 6:
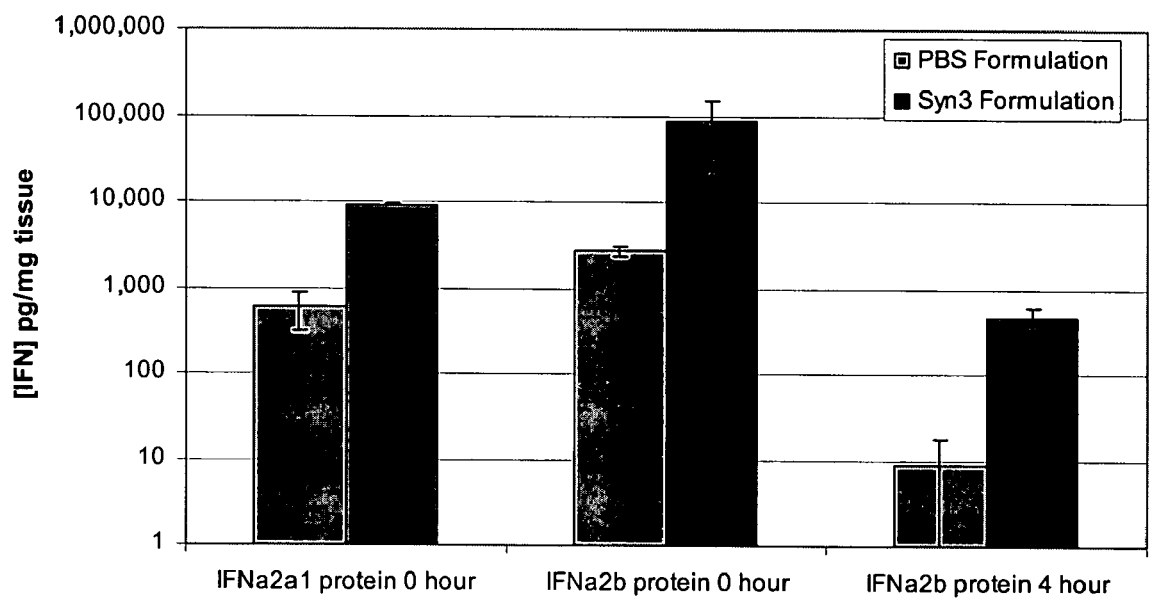

Final Concentrations of the Excipients:
SYN3: (120 mg/20 ml)/6=1 mg/ml
Citric Acid Monohydrate: (1.6 mg/20 ml)/6=0.01333 mg/ml
Sodium Citrate Dihydrate: (5.1 mg/20 ml)/6=0.0425 mg/ml
Hydoxy-cyclodextrin: (1000 mg/20 ml)/6=8.33 mg/ml
Polysorbate 80 (Tween-80): (60 mg/20 ml)/6=0.5 mg/ml The amounts of IFNα2b present in tissue homogenates was determined using an ELISA assay (PBL). The concentration of protein was measured using a Bradford protein assay. The levels of IFN present in the tissue was expressed as pg IFN/mg tissue. As shown in FIG. 5, delivery of IFNα2b in a SYN3 formulation resulted in approximately a 15-fold increase in the amount of detectable IFNα2b protein up to 24 hours after treatment. FIG. 6 shows specific time points. Moreover, the delivery of the hybrid IFN protein (IFNβ2α1) was also enhanced by delivery in the SYN3 formulation, and was detected at similar levels tissue concentrations as the IFNα2b protein.

Example 4

Analysis of Interferon Biological Effects on Bladder Urothelium After Administration of IFN Protein in a SYN3 (FIG. 4 Compound 8) Formulation This example investigated if the increase in IFN tissue concentrations resulted in measurable biological responses. To assess biological activity, we used RT-PCR to monitor the expression of IFN responsive genes in rat bladder homogenates after treatment with IFN protein (both Intron A and the 'universal' interferon (IFN A/D; IFNα2α1). The following rat genes were assayed: 2',5'-oligoadenylate synthetase (2', 5'-OAS); the gene encoding the interferon-induced p78 protein (MxAMX1) (MX1); Interferon Regulatory Factor 1 (IRF-1); and Interferony IFNγ. (IFNγ is not normally considered an IFN response gene, but is usually expressed after exposure to pathogens such as BCG and can be induced by recombinant adenoviruses). The methods were generally described as above in Example 3. After 1 hour, the test articles were removed and the animals allowed to recover in the home cage. Rats were sacrificed at the times indicated (0 hour=immediately after the treatment) and the samples were snap-frozen in liquid N2 and submitted for RT-PCR analysis.

| Group | Animal ID's | Sacrifice time | Treatment |
|---|---|---|---|
| 1 | 193, 194 | 0 h post tx | IFN α2b protein in PBS |
| 2 | 176, 177 | 4 h post tx | IFN α2b protein in PBS |
| 3 | 185, 186 | 1 d post tx | IFN α2b protein in PBS |
| 4 | 190, 191, 192 | 0 h post tx | IFN α2b protein in SYN3: 1 mg/ml |
| 5 | 178, 179, 180 | 4 h post tx | IFN α2b protein in SYN3: 1 mg/ml |
| 6 | 187, 188, 189 | 1 d post tx | IFN α2b protein in SYN3: 1 mg/ml |
| 7 | 181, 182 | 4 h post tx | IACB: $1 \times 10^{11}$ P/ml in SYN3: 1 mg/ml |
| 8 | 183, 184 | 1 d post tx | IACB: $1 \times 10^{11}$ P/ml in SYN3: 1 mg/ml |
| 1 | 293, 294 | 0 h post tx | IFN α2α1 protein in PBS |
| 2 | 276, 277 | 4 h post tx | IFN α2α1 protein in PBS |
| 3 | 285, 286 | 1 d post tx | IFN α2α1 protein in PBS |
| 4 | 290, 291, 292 | 0 h post tx | IFN α2α1 protein in SYN3: 1 mg/ml |
| 5 | 278, 279, 280 | 4 h post tx | IFN α2α1 protein in SYN3: 1 mg/ml |
| 6 | 287, 288, 289 | 1 d post tx | IFN α2α1 protein in SYN3: 1 mg/ml |
| 7 | 281, 282 | 4 h post tx | IHCB: $1 \times 10^{11}$ P/ml in SYN3: 1 mg/ml |
| 8 | 283, 284 | 1 d post tx | IHCB: $1 \times 10^{11}$ P/ml in SYN3: 1 mg/ml |

Materials Needed:
38female Harlan Sprague-Dawley rats; transferred from protocol 04-634
ICAB: Tris-glycerol formulation $7.57 \times 10^{11}$ P/ml
IHCB: vPBS formulation $1.10 \times 10^{12}$ P/ml
SYN3: 6× stock (6 mg/ml)
D-PBS
Tris-glycerol buffer:
Sterile WFI
IFN α2α1 protein: 105 μg/ml=$105 \times 10^6$ pg/ml
  $1.34 \times 10^7$ IU/ml
  $1.28 \times 10^8$ IU/mg Preparation of Test Articles:

1) IFNα2b/PBS: 5 ml @ 2 MIU/ml Final Concentration
   Hydrate one reference vial (10 MIU/vial) in 1 ml sterile water for injection 1,000 μl Intron A concentrate 4,000 μl PBS 2) IFN α2b/SYN3: 10 ml @ 2 MIU/ml Final Concentration
   Hydrate two reference vials with 2 ml sterile water for injection 2,000 μl Intron A concentrate 6,334 μl PBS 1,666 μl SYN3

IACB/SYN3: 4.5 ml @ $1.0 \times 10^{11}$ P/ml in SYN3
660 μl IACB
750 μl SYN3
3,090 μl Tris-glycerol buffer IFNα2α/PBS: 4 ml @ 1 MIU/ml Final Concentration
298 μl IFNα2α1 protein
3,702 μl PBS IFNα2α1/SYN3: 6 ml @ 1 MIU/ml Final Concentration 444 μl IFNα2α1 protein 4,556 μl PBS 1,000 μl SYN3

IHCB/SYN3 4.0 ml @ $1.0 \times 10^{11}$ P/ml in SYN3

364 μl IHCB

667 μl SYN3

2,969 μl Tris-glycerol buffer

The animals were sacrificed and their bladders harvested on liquid nitrogen for RT-PCR analysis. The primary analysis was to compare the levels of mRNA for the above genes to the level that is observed after Intron A/PBS delivery. The level of gene activation was normalized to the Intron A/PBS group (1.0).

The results indicated that the addition of SYN3 increased the expression of known downstream IFN-activated genes (2'-5'OAS, MX1) compared to delivery of the same amount of protein in a PBS formulation. The hybrid protein in SYN3 (BS: IFNα2α1/SYN3) appeared to provide more potent biological responses even though it was dosed at 1 MIU/ml instead of the 2 MIU/ml for the IFNα2b. While both Intron A (IFNα2b) and the hybrid IFN (IFNα2α1) increased the expression of the rat OAS and MX1 genes when administered in a SYN3 formulation, both were somewhat inferior to the levels obtained after administration of rAd-IFNα2b or rAd-IFNα2α1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula I:

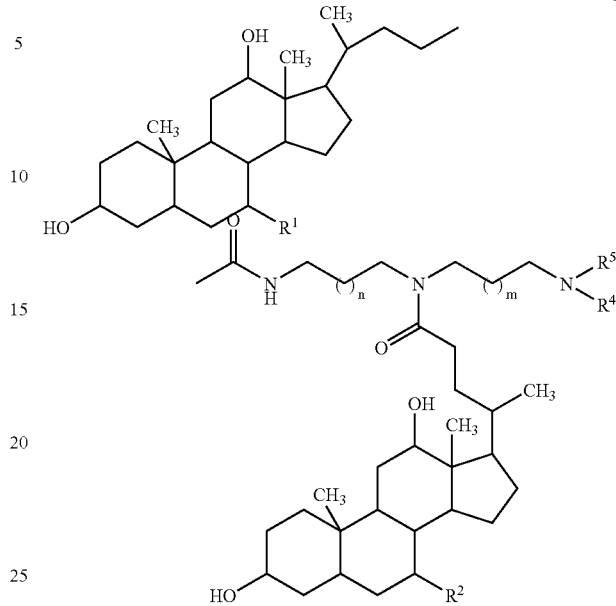

wherein:
$R^1$ and $R^2$ are each independently a member selected from the group consisting of hydrogen, and a hydroxyl group;
m and n are each independently selected from about 0-2;
wherein $R^4$ and $R^5$ are each independently a member selected from the group consisting of a saccharide residue, an optionally substituted alkyl, an optionally substituted acyl, an optionally substituted acyloxy.

2. The compound of claim 1, wherein $R^1$ and $R^2$ are both hydroxyl groups.

3. The compound of claim 1, wherein m and n are each 1.

4. The compound of claim 3, wherein said compound has Formula II:

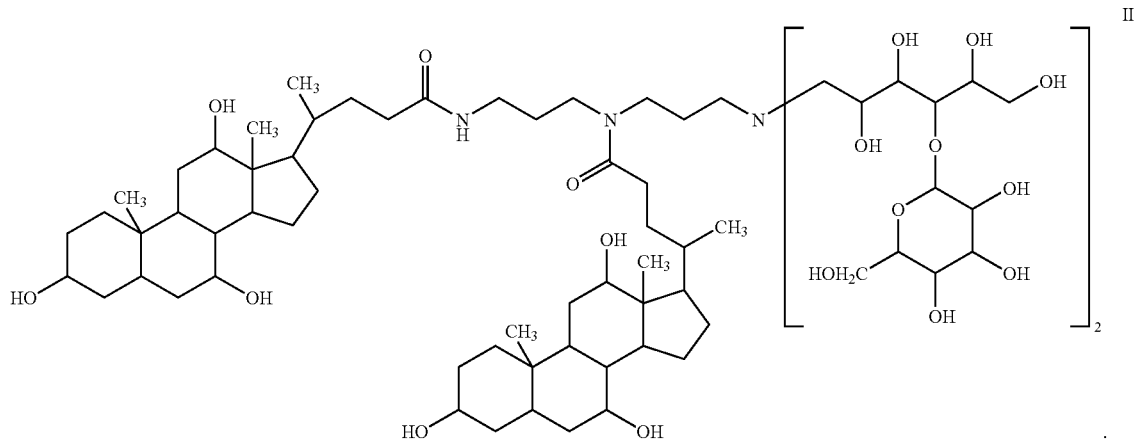

5. The compound of claim 1, wherein $R^4$ and $R^5$ are independently a saccharide residue.

6. The compound of claim 3, wherein $R^4$ and $R^5$ are independently an optionally substituted acyl.

7. The compound of claim 1, wherein $R^5$ is succinyl.

8. The compound of claim 1, wherein $R^5$ is acyloxy.

9. The compound of claim 1, wherein $R^4$ and $R^5$ are independently an optionally substituted alkyl.

10. The compound of claim 1, wherein $R^4$ and $R^5$ are independently an optionally substituted-acyloxy.

11. A composition for delivering an agent to a cell, the composition comprising the agent and a delivery enhancing compound of Formula I:

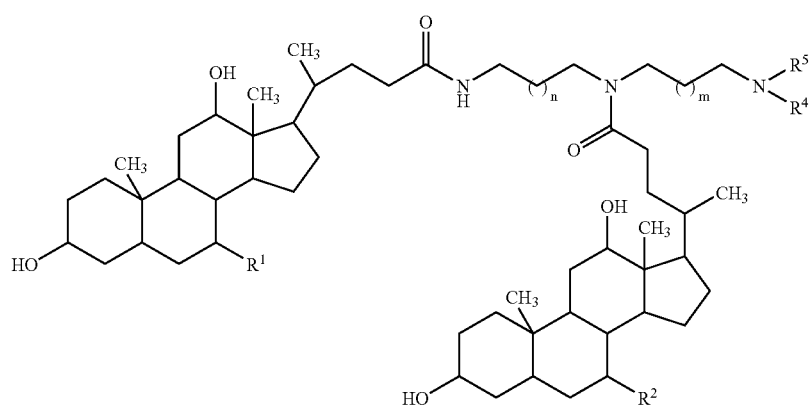

wherein:
  $R^1$ and $R^2$ are each independently a member selected from the group consisting of hydrogen, and a hydroxyl group;
  m and n are each independently selected from about 0-2;
  wherein $R^4$ and $R^5$ are each independently a member selected from the group consisting of a saccharide residue, an optionally substituted alkyl, an optionally substituted acyl, an optionally substituted acyloxy.

12. The composition according to claim 11, wherein $R^1$ and $R^2$ are both hydroxyl groups.

13. The composition according to claim 11, wherein m and n are each 1.

14. The composition according to claim 13, wherein said composition has Formula II:

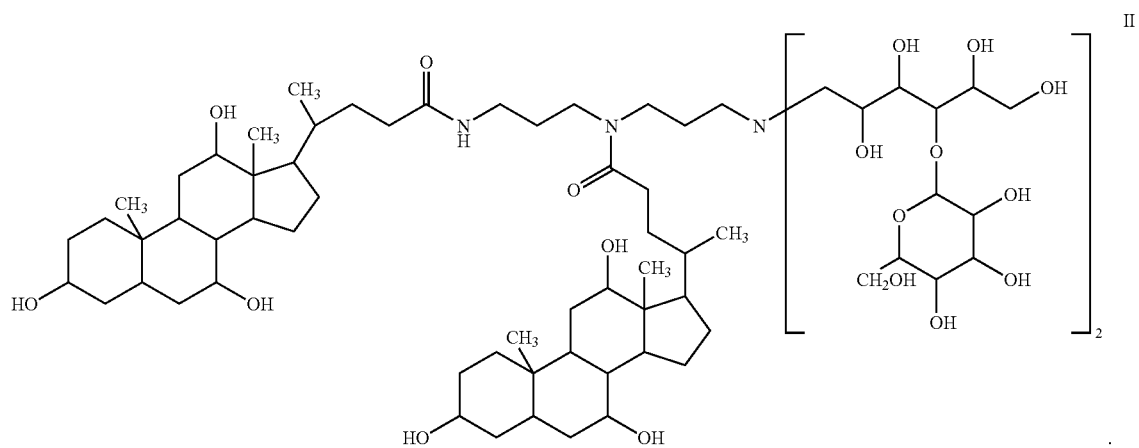

15. The composition according to claim 11, wherein $R^4$ and $R^5$ are independently a saccharide residue.

16. The composition according to claim 11, wherein $R^4$ and $R^5$ are independently an optionally substituted acyl.

17. The composition according to claim 11, wherein $R^5$ is succinyl.

18. The composition according to claim 11, wherein $R^5$ is acyloxy.

19. The composition according to claim 11, wherein $R^4$ and $R^5$ are independently an optionally substituted alkyl.

20. The composition according to claim 11, wherein $R^4$ and $R^5$ are independently an optionally substituted acyloxy.

21. The composition according to claim 11, wherein said agent is a diagnostic agent.

22. The composition according to claim 11, wherein said agent modulates a biological process in a cell when the agent is present in the cell.

23. The composition according to claim 22, wherein the biological process is selected from the group consisting of cell growth, differentiation, proliferation, a metabolic or biosynthetic pathway, gene expression, a disease-associated process, and an immune response.

24. The composition according to claim 11, wherein said agent comprises a polynucleotide or protein.

25. The composition according to claim 24, wherein said polynucleotide is selected from the group consisting of an antisense nucleic acid, a triplex-forming nucleic acid, and a nucleic acid that comprises a gene which encodes a polypeptide that modulates a biological process.

26. The composition according to claim 25, wherein the gene is a tumor suppressor gene.

27. The composition according to claim 26, wherein the tumor suppressor gene is selected from the group consisting of a retinoblastoma gene and a p53 gene.

28. The composition according to claim 11, wherein the composition further comprises a polymeric matrix.

29. The composition according to claim 11, wherein the composition further comprises a mucoadhesive.

30. The composition according to claim 24, wherein said agent comprises a protein.

31. The composition according to claim 30, wherein said protein is an interferon.

32. The method of claim 31, wherein the interferon is selected from the group consisting of interferon-α, interferon-β, interferon-δ, and interferon-γ, and a fusion interferon thereof.

33. The method of claim 31, wherein the interferon is selected from the group consisting of interferon α-2β, a fusion interferon is α-/2α-1, and interferon α-2e.

34. The method of claim 31, wherein the interferon is human α1 or α2 interferon.

35. The composition according to claim 30, wherein said protein is an antibody.

36. The composition according to claim 35, wherein said antibody is selected from the group consisting of anti-interferon-α, anti-interferon-β, anti-interferon-δ, anti-interferon-γ, an anti-interleukin, anti-IL-1, anti-IL-2, anti-IL-4, anti-Il-6, anti-IL-7 and anti-IL-10.

37. A method of delivering an agent to a cell in an epithelial tissue, said method comprising locally administering to said tissue a composition comprising the agent and a compound of claim 1.

38. A method of treating superficial bladder cancer of the urinary bladder by intravesical administration to a mammalian subject of a recombinant viral vector encoding a cytostatic or tumor suppressor gene in combination with a compound of claim 1.

39. The method of claim 38, wherein said tumor suppressor gene is selected from the group consisting of RB56, RB110, RB94, P53, and P53 delta13-19.

40. The method of claim 38, wherein said cytostatic gene is a gene for interferon.

41. The method of claim 40, wherein the interferon is selected from the group consisting of interferon-α, interferon-β, interferon-δ, and interferon-γ, and a fusion interferon thereof.

42. The method of claim 40, wherein the interferon is selected from the group consisting of interferon α-2β, a fusion interferon is α-/2α-1, and interferon α-2e.

43. The method of claim 40, wherein the interferon is human α1 or α2 interferon.

44. The method of claim 38, wherein said compound of Formula I further comprises a solubilizing agent.

45. The method of claim 37, wherein the agent is a therapeutic agent.

46. The method of claim 37, wherein the agent is a diagnostic agent.

47. The method of claim 37, wherein the concentration of the delivery enhancing compound is about 0.002 to about 2 mg/ml.

48. The method of claim 47, wherein the concentration of the delivery enhancing compound is about 0.02 to about 2 mg/ml.

49. The method of claim 48, wherein the concentration of the delivery enhancing compound is about 0.2 to 2 mg/ml.

50. The method of claim 37, wherein the delivery-enhancing compound is soluble in an aqueous solution in the absence of a detergent other than the delivery-enhancing compound.

51. The method of claim 50, wherein the solubility of the delivery-enhancing compound in aqueous solution is at least about 1 mg/ml in the absence of a detergent other than the delivery-enhancing compound.

52. The method of claim 37, wherein the agent is delivered across a glycosaminoglycan (GAG) layer.

53. The method of claim 37, wherein the epithelial tissue is selected from the group consisting of gastrointestinal tract, skin, lung, and mucosa.

54. The method of claim 37, wherein the administration is by intravesical administration.

55. The method of claim 37, wherein the agent is a protein.

56. The method of claim 37, wherein the agent is a gene.

57. The method of claim 56, wherein the gene is administered in a vector.

58. The method of claim 57, wherein the vector is a viral vector.

59. The method of claim 58, wherein the viral vector is selected from the group consisting of an adenoviral vector, a retroviral vector, and an adeno-associated viral vector.

60. The method of claim 58, wherein the viral vector is administered as a suspension having a viral vector concentration of from $1\times10^8$ particles/ml to $5\times10^{11}$ particles/ml.

61. The method of claim 60, wherein the viral vector concentration in the suspension is from $1\times10^9$ particles/ml to $1\times10^{11}$ particles/ml.

62. The method of claim 56, wherein the gene is a therapeutic gene.

63. The method of claim 62, wherein the therapeutic gene is a tumor suppressor gene.

64. The method of claim 63, wherein the tumor suppressor gene is a p53 gene.

65. The method of claim 63, wherein the tumor suppressor gene is a retinoblastoma gene.

66. The method of claim 65, wherein the retinoblastoma tumor suppressor gene encodes full length RB protein.

67. The method of claim 65, wherein the retinoblastoma tumor suppressor gene encodes $p56^{RB}$.

68. The method of claim 62, wherein the cells are cancer cells.

69. The method of claim 68, wherein the cancer cells are bladder cancer cells.

70. The method of claim 68, wherein the cancer cells are provided as a tissue.

71. The method of claim 38, wherein the delivery-enhancing compound is administered prior to administration of the agent.

72. The method of claim 38, wherein the delivery enhancing compound is administered with the agent.

\* \* \* \* \*

UNITED STATES PATENT AND TRADEMARK OFFICE
CERTIFICATE OF CORRECTION

PATENT NO.        : 7,355,056 B2
APPLICATION NO.   : 10/861545
DATED             : April 8, 2008
INVENTOR(S)       : Connor et al.

It is certified that error appears in the above-identified patent and that said Letters Patent is hereby corrected as shown below:

In the specification:

Column 25, Line 48, please delete "5" and insert -- 5 --
Column 27, Line 42, please delete "(IFNβ2α1)" and insert -- (IFNα2α1) --
Column 27, Line 61, please delete "Interferony" and insert -- Interferonγ --

In the claims:

Column 30, Claim 1, please delete the printed figure and replace it with

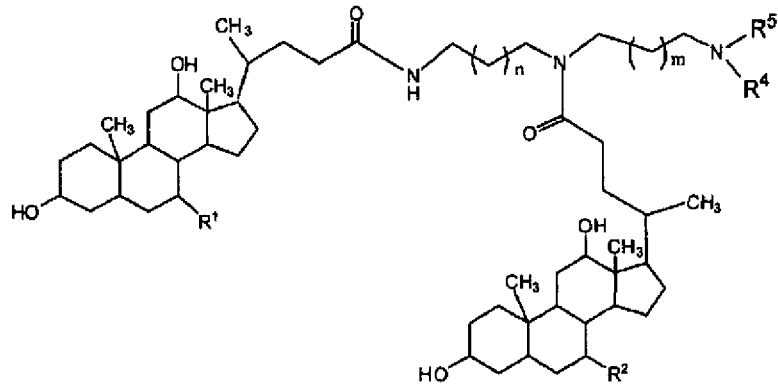

Column 33, Claim 32, Line 49, please delete "method" and insert -- composition --
Column 33, Claim 33, Line 54, please delete "method" and insert -- composition --
Column 33, Claim 34, Line 57, please delete "method" and insert -- composition --

Signed and Sealed this

Fifth Day of January, 2010

David J. Kappos
Director of the United States Patent and Trademark Office